US012415847B2

(12) United States Patent
Hla et al.

(10) Patent No.: US 12,415,847 B2
(45) Date of Patent: Sep. 16, 2025

(54) ApoM-Fc FUSION PROTEINS FOR TREATING LUNG DISEASES

(71) Applicant: Children's Medical Center Corporation, Boston, MA (US)

(72) Inventors: Timothy T. Hla, Wellesley, MA (US); Steven L. Swendeman, Cambridge, MA (US); Mark Puder, Medfield, MA (US); Lois Smith, West Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 70 days.

(21) Appl. No.: 17/284,299

(22) PCT Filed: Oct. 11, 2019

(86) PCT No.: PCT/US2019/055831
§ 371 (c)(1),
(2) Date: Apr. 9, 2021

(87) PCT Pub. No.: WO2020/077206
PCT Pub. Date: Apr. 16, 2020

(65) Prior Publication Data
US 2021/0380665 A1    Dec. 9, 2021

Related U.S. Application Data

(60) Provisional application No. 62/744,903, filed on Oct. 12, 2018.

(51) Int. Cl.
*A61P 11/00* (2006.01)
*C07K 14/775* (2006.01)
*A61K 38/00* (2006.01)

(52) U.S. Cl.
CPC ............ *C07K 14/775* (2013.01); *A61P 11/00* (2018.01); *A61K 38/00* (2013.01); *C07K 2319/30* (2013.01)

(58) Field of Classification Search
CPC .............. C07K 14/775; C07K 2319/30; A61K 38/00; A61P 11/00
See application file for complete search history.

(56) References Cited

U.S. PATENT DOCUMENTS

| 10,870,689 B2 | 12/2020 | Hla et al. |
| 2011/0178029 A1 | 7/2011 | Knudsen et al. |
| 2013/0195849 A1 | 8/2013 | Spreter Von et al. |
| 2013/0324701 A1 | 12/2013 | Williams et al. |
| 2014/0303086 A1 | 10/2014 | Hla et al. |
| 2016/0184458 A1* | 6/2016 | Heartlein ........... A61K 48/0075 514/44 R |
| 2017/0360749 A1 | 12/2017 | Harijith et al. |
| 2019/0185545 A1 | 6/2019 | Hla et al. |
| 2021/0032310 A1 | 2/2021 | Hla et al. |

FOREIGN PATENT DOCUMENTS

| CN | 1556409 A | 1/2004 |
| CN | 101557817 A | 10/2009 |
| CN | 102858985 A | 1/2013 |
| CN | 105175553 A | 12/2015 |
| JP | 2020-531010 A | 11/2020 |
| WO | WO 2006/000448 A2 | 1/2006 |
| WO | WO 2010/049103 A1 | 5/2010 |
| WO | WO 2012/162392 A1 | 11/2012 |
| WO | WO 2017/031353 A1 | 2/2017 |
| WO | WO 2018/052615 A1 | 3/2018 |
| WO | WO 2019/035931 A1 | 2/2019 |

OTHER PUBLICATIONS

Andersson-Sjoland et al., ROS-induced endothelial stress contributes to pulmonary fibrosis through pericytes and Wnt signaling, Laboratory Investigation; 96: 206-217. (Year: 2016).*
Zhaorigetu et al., Perturbations in Endothelial Dysfunction-Associated Pathways in the Nitrofen-Induced Congenital Diaphragmatic Hernia Model, Journal of Vascular Research; 55: 26-34 (Abstract). (Year: 2017).*
Green, The role of the endothelium in asthma and chronic obstructive pulmonary disease (COPD), Respiratory Research; 18(20). (Year: 2017).*
Gorshkova et al., Inhibition of serine palmitoyltransferase delays the onset of radiation-induced pulmonary fibrosis through the negative regulation of sphingosine kinase-1 expression, Journal of Lipid Research vol. 53. (Year: 2012).*
Harajith et al. Sphingosine Kinase 1 Deficiency Confers Protection against Hyperoxia-Induced Bronchopulmonary Dysplasia in a Murine Model Role of S1P Signaling and Nox Proteins, The American Journal of Pathology, vol. 183, No. 4, http://dx.doi.org/10.1016/j.ajpath.2013.06.018 (Year: 2013).*
Chen et al., The Sphingosine Kinase 1/Sphingosine-1-Phosphate Pathway in Pulmonary Arterial Hypertension,American Journal of Respiratory and Critical Care Medicine vol. 190 No. 9. (Year: 2014).*
Burg et al., Sphingosine-1 Phosphate Receptor-i-Mediated Endothelial Cell Barrier Function Protects Against Immune Complex-Induced Vascular Injury: A Potential Novel Therapeutic Target for SLE. Abstract 1790. 2017 ACR/ARHP Annual Meeting. Sep. 18 (Year: 2017).*
Kho et al., Am J Physiol Lung Cell Mol Physiol 305: L542-L554; doi: 10.1152/ajplung.00403.2012 (Year: 2013).*
Hopkinsmedicine.org_-_BPD.pdf; examiner generated from: https://www.hopkinsmedicine.org/health/conditions-and-diseases/bronchopulmonary-dysplasia (Year: 2024).*
Hopkinsmedicine.org_-_CDH.pdf; examiner generated from: https://www.hopkinsmedicine.org/health/conditions-and-diseases/congenital-diaphragmatic-hernia (Year: 2024).*
Burg et al., Sphingosine 1-Phosphate Receptor 1 Signaling Maintains Endothelial Cell Barrier Function and Protects Against Immune Complex-Induced Vascular Injury. Arthritis Rheumatol. Nov. 2018;70(11):1879-1889.

(Continued)

*Primary Examiner* — Catherine S Hibbert
(74) *Attorney, Agent, or Firm* — Wolf, Greenfield & Sacks, P.C.

(57) ABSTRACT

Provided herein are methods of treating lung disease using fusion proteins comprising ApoM (e.g., human or murine ApoM) fused to a constant region (Fc) of a immunoglobulin G (IgG, e.g., human IgG or murine IgG).

22 Claims, 4 Drawing Sheets

Specification includes a Sequence Listing.

(56) References Cited

OTHER PUBLICATIONS

Christoffersen et al., Endothelium-protective sphingosine-1-phosphate provided by HDL-associated apolipoprotein M. Proc Natl Acad Sci U S A. Jun. 7, 2011;108(23):9613-8.
Kaplan et al., TRAIL (Apo2 ligand) and TWEAK (Apo3 ligand) mediate CD4+ T cell killing of antigen-presenting macrophages. J Immunol. Mar. 15, 2000;164(6):2897-904.
Snoek et al., Sphingolipids in Congenital Diaphragmatic Hernia; Results from an International Multicenter Study. PLOS One. May 9, 2016;11(5).
Swendemen et al., An engineered S1P chaperone attenuates hypertension and ischemic injury. Sci Signal. Aug. 15, 2017;10(492).
Wang et al., Immunoglobulin Fc domain fusion to TRAIL significantly prolongs its plasma half-life and enhances its antitumor activity. Mol Cancer Ther. Mar. 2014;13(3):643-50.
Wu et al., Pharmacokinetics of Peptide-Fc fusion proteins. J Pharm Sci. Jan. 2014;103(1):53-64. doi: 10.1002/jps.23783. Epub Nov. 27, 2013.
Yu et al., Immunoglobulin Fc domain fusion to apolipoprotein (a) kringle V significantly prolongs plasma half-life without affecting its anti-angiogenic activity. Protein Eng Des Sel. Jun. 2013;26(6):425-32.
Zauner et al., Glycoproteomic analysis of antibodies. Mol Cell Proteomics. Apr. 2013;12 (4):856-65.
[No Author Listed] NCBI Protein Blast Sequence Comparison. Performed on Apr. 8, 2022. 1 page.
[No Author Listed] UniProt Database Accession No. P01857. UniProtKB-P01857 (IGHG1_Human). Immunoglobulin heavy constant gamma 1. First Available 1986. 20 pages.
[No Author Listed] Cambridge English Dictionary: "Artificial". Accessed Dec. 19, 2022. 7 pages. https://dictionary.cambridge.org/us/dictionary /english/artificial.
[No Author Listed] GenBank Accession No. NP_061974.2. Apolipoprotein M Isoform 1. *Homo sapiens*. Accessed on Mar. 25, 2022. 3 pages.
[No Author Listed] GenBank Accession No. NP_061286.1. Apolipoprotein M Precursor. *Mus musculus*. Accessed on Mar. 25, 2022. 3 pages.
Burg et al., Sphingosine-1 Phosphate Receptor-1-Mediated Endothelial Cell Barrier Function Protects Against Immune Complex-Induced Vascular Injury: A Potential Novel Therapeutic Target for SLE. Abstract 1790. 2017 ACR/ARHP Annual Meeting. Sep. 18, 2017.
Christoffersen et al., The signal peptide anchors apolipoprotein M in plasma lipoproteins and prevents rapid clearance of apolipoprotein M from plasma. J Biol Chem. Jul. 4, 2008;283(27):18765-72.
Zhaorigetu et al., Perturbations in Endothelial Dysfunction-Associated Pathways in the Nitrofen-Induced Congenital Diaphragmatic Hernia Model. J Vasc Res. 2018;55(1):26-34. doi: 10.1159/000484087. Epub Dec. 8, 2017.
CN 201880066972.7, Apr. 1, 2023, Chinese Office Action.
CN 201880066972.7, Nov. 23, 2023, Chinese Office Action.
CN 201780056922.6, Mar. 17, 2023, Chinese Office Action.
CN 201780056922.6, Jul. 7, 2023, Chinese Office Action.
Chen et al., Expression of human cytokines dramatically improves reconstitution of specific human-blood lineage cells in humanized mice. Proc Natl Acad Sci U S A. Dec. 22, 2009;106(51):21783-8. doi: 10.1073/pnas.0912274106. Epub Dec. 4, 2009.
Sloud et al., Generation of new peptide-Fc fusion proteins that mediate antibody-dependent cellular cytotoxicity against different types of cancer cells. Mol Ther Methods Clin Dev. Nov. 4, 2015;2:15043. doi: 10.1038/mtm.2015.43. eCollection 2015.

* cited by examiner

S1P1 Gi activation

SEQUENCE LISTING

```
<160> NUMBER OF SEQ ID NOS: 28

<210> SEQ ID NO 1
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 1

Met Tyr Arg Met Gln Leu Leu Ser Cys Ile Ala Leu Ser Leu Ala Leu
1               5                   10                  15

Val Thr Asn Ser Ile Ser Arg Val Tyr Gln Cys Pro Glu His Ser Gln
                20                  25                  30

Leu Thr Thr Leu Gly Val Asp Gly Lys Glu Phe Pro Glu Val His Leu
            35                  40                  45

Gly Gln Trp Tyr Phe Ile Ala Gly Ala Ala Pro Thr Lys Glu Glu Leu
        50                  55                  60

Ala Thr Phe Asp Pro Val Asp Asn Ile Val Phe Asn Met Ala Ala Gly
65                  70                  75                  80

Ser Ala Pro Met Gln Leu His Leu Arg Ala Thr Ile Arg Met Lys Asp
                85                  90                  95

Gly Leu Cys Val Pro Arg Lys Trp Ile Tyr His Leu Thr Glu Gly Ser
            100                 105                 110

Thr Asp Leu Arg Thr Glu Gly Arg Pro Asp Met Lys Thr Glu Leu Phe
        115                 120                 125

Ser Ser Ser Cys Pro Gly Gly Ile Met Leu Asn Glu Thr Gly Gln Gly
    130                 135                 140

Tyr Gln Arg Phe Leu Leu Tyr Asn Arg Ser Pro His Pro Pro Glu Lys
145                 150                 155                 160

Cys Val Glu Glu Phe Lys Ser Leu Thr Ser Cys Leu Asp Ser Lys Ala
                165                 170                 175

Phe Leu Leu Thr Pro Arg Asn Gln Glu Ala Cys Glu Leu Ser Asn Asn
            180                 185                 190

Trp Ala Ser Thr Lys Gly Pro Ser Val Phe Pro Leu Ala Pro Ser Ser
        195                 200                 205

Lys Ser Thr Ser Gly Gly Thr Ala Ala Leu Gly Cys Leu Val Lys Asp
    210                 215                 220
```

```
Tyr Phe Pro Glu Pro Val Thr Val Ser Trp Asn Ser Gly Ala Leu Thr
225                 230                 235                 240

Ser Gly Val His Thr Phe Pro Ala Val Leu Gln Ser Ser Gly Leu Tyr
            245                 250                 255

Ser Leu Ser Ser Val Val Thr Val Pro Ser Ser Ser Leu Gly Thr Gln
            260                 265                 270

Thr Tyr Ile Cys Asn Val Asn His Lys Pro Ser Asn Thr Lys Val Asp
            275                 280                 285

Lys Lys Val Glu Pro Lys Ser Cys Asp Lys Thr His Thr Cys Pro Pro
290                 295                 300

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
            325                 330                 335

Cys Val Val Val Asp Val Ser His Glu Asp Pro Glu Val Lys Phe Asn
            340                 345                 350

Trp Tyr Val Asp Gly Val Glu Val His Asn Ala Lys Thr Lys Pro Arg
            355                 360                 365

Glu Glu Gln Tyr Asn Ser Thr Tyr Arg Val Val Ser Val Leu Thr Val
370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
            405                 410                 415

Gly Gln Pro Arg Glu Pro Gln Val Tyr Thr Leu Pro Pro Ser Arg Glu
            420                 425                 430

Glu Met Thr Lys Asn Gln Val Ser Leu Thr Cys Leu Val Lys Gly Phe
            435                 440                 445

Tyr Pro Ser Asp Ile Ala Val Glu Trp Glu Ser Asn Gly Gln Pro Glu
            450                 455                 460

Asn Asn Tyr Lys Thr Thr Pro Pro Val Leu Asp Ser Asp Gly Ser Phe
465                 470                 475                 480

Phe Leu Tyr Ser Lys Leu Thr Val Asp Lys Ser Arg Trp Gln Gln Gly
            485                 490                 495

Asn Val Phe Ser Cys Ser Val Met His Glu Ala Leu His Asn His Tyr
            500                 505                 510

Thr Gln Lys Ser Leu Ser Leu Ser Pro Gly Lys
            515                 520

<210> SEQ ID NO 2
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 2

Met Tyr Arg Met Gln Leu Leu Ser Cys Ile Ala Leu Ser Leu Ala Leu
1               5                   10                  15

Val Thr Asn Ser Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
            35                  40                  45

Phe Ile Ala Gly Ala Ala Pro Thr Thr Glu Glu Leu Ala Thr Phe Asp
        50                  55                  60
```

```
Pro Val Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
        115                 120                 125

Ser Cys Pro Gly Gly Ile Met Leu Lys Glu Thr Gly Gln Gly Tyr Gln
    130                 135                 140

Arg Phe Leu Leu Tyr Asn Arg Ser Pro His Pro Glu Lys Cys Val
145                 150                 155                 160

Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ile
            180                 185                 190

Ser Ser Ala Ser Ser Ala Lys Thr Thr Pro Pro Ser Val Tyr Pro Leu
        195                 200                 205

Ala Pro Gly Ser Ala Ala Gln Thr Asn Ser Met Val Thr Leu Gly Cys
210                 215                 220

Leu Val Lys Gly Tyr Phe Pro Glu Pro Val Thr Val Thr Trp Asn Ser
225                 230                 235                 240

Gly Ser Leu Ser Ser Gly Val His Thr Phe Pro Ala Val Leu Gln Ser
            245                 250                 255

Asp Leu Tyr Thr Leu Ser Ser Ser Val Thr Val Pro Ser Ser Thr Trp
        260                 265                 270

Pro Ser Glu Thr Val Thr Cys Asn Val Ala His Pro Ala Ser Ser Thr
    275                 280                 285

Lys Val Asp Lys Lys Ile Val Pro Arg Asp Cys Gly Cys Lys Pro Cys
290                 295                 300

Ile Cys Thr Val Pro Glu Val Ser Ser Val Phe Ile Phe Pro Pro Lys
305                 310                 315                 320

Pro Lys Asp Val Leu Thr Ile Thr Leu Thr Pro Lys Val Thr Cys Val
            325                 330                 335

Val Val Asp Ile Ser Lys Asp Asp Pro Glu Val Gln Phe Ser Trp Phe
        340                 345                 350

Val Asp Asp Val Glu Val His Thr Ala Gln Thr Gln Pro Arg Glu Glu
    355                 360                 365

Gln Phe Asn Ser Thr Phe Arg Ser Val Ser Glu Leu Pro Ile Met His
    370                 375                 380

Gln Asp Trp Leu Asn Gly Lys Glu Phe Lys Cys Arg Val Asn Ser Ala
385                 390                 395                 400

Ala Phe Pro Ala Pro Ile Glu Lys Thr Ile Ser Lys Thr Lys Gly Arg
            405                 410                 415

Pro Lys Ala Pro Gln Val Tyr Thr Ile Pro Pro Lys Glu Gln Met
        420                 425                 430

Ala Lys Asp Lys Val Ser Leu Thr Cys Met Ile Thr Asp Phe Phe Pro
        435                 440                 445

Glu Asp Ile Thr Val Glu Trp Gln Trp Asn Gly Gln Pro Ala Glu Asn
    450                 455                 460

Tyr Lys Asn Thr Gln Pro Ile Met Asp Thr Asp Gly Ser Tyr Phe Val
465                 470                 475                 480
```

```
Tyr Ser Lys Leu Asn Val Gln Lys Ser Asn Trp Glu Ala Gly Asn Thr
            485                 490                 495
Phe Thr Cys Ser Val Leu His Glu Gly Leu His Asn His Thr Glu
        500                 505                 510
Lys Ser Leu Ser His Ser Pro Gly Lys
        515                 520
```

<210> SEQ ID NO 3
<211> LENGTH: 523
<212> TYPE: PRT
<213> ORGANISM: Artificial Sequence
<220> FEATURE:
<223> OTHER INFORMATION: Synthetic polypeptide

<400> SEQUENCE: 3

```
Met Tyr Arg Met Gln Leu Leu Ser Cys Ile Ala Leu Ser Leu Ala Leu
1               5                   10                  15
Val Thr Asn Ser Ile Ser Arg Val Tyr Gln Cys Pro Glu His Ser Gln
            20                  25                  30
Leu Thr Thr Leu Gly Val Asp Gly Lys Glu Phe Pro Glu Val His Leu
        35                  40                  45
Gly Gln Trp Tyr Phe Ile Ala Gly Ala Ala Pro Thr Lys Glu Glu Leu
    50                  55                  60
Ala Thr Phe Asp Pro Val Asp Asn Ile Val Phe Asn Met Ala Ala Gly
65                  70                  75                  80
Ser Ala Pro Met Gln Leu His Leu Arg Ala Thr Ile Arg Met Lys Asp
                85                  90                  95
Gly Leu Cys Val Pro Arg Lys Trp Ile Tyr His Leu Thr Glu Gly Ser
            100                 105                 110
Thr Asp Leu Arg Thr Glu Gly Arg Pro Asp Met Lys Thr Glu Leu Phe
        115                 120                 125
Ser Ser Ser Cys Pro Gly Gly Ile Met Leu Asn Glu Thr Gly Gln Gly
    130                 135                 140
Tyr Gln Arg Phe Leu Leu Tyr Asn Arg Ser Pro His Pro Pro Glu Lys
145                 150                 155                 160
Cys Val Glu Glu Phe Lys Ser Leu Thr Ser Cys Leu Asp Ser Lys Ala
                165                 170                 175
Phe Leu Leu Thr Pro Arg Asn Gln Glu Ala Cys Glu Leu Ser Asn Asn
            180                 185                 190
Trp Ile Ser Ser Ala Ser Ala Lys Thr Thr Pro Pro Ser Val Tyr
        195                 200                 205
Pro Leu Ala Pro Gly Ser Ala Ala Gln Thr Asn Ser Met Val Thr Leu
    210                 215                 220
Gly Cys Leu Val Lys Gly Tyr Phe Pro Glu Pro Val Thr Val Thr Trp
225                 230                 235                 240
Asn Ser Gly Ser Leu Ser Ser Gly Val His Thr Phe Pro Ala Val Leu
                245                 250                 255
Gln Ser Asp Leu Tyr Thr Leu Ser Ser Val Thr Val Pro Ser Ser
            260                 265                 270
Thr Trp Pro Ser Glu Thr Val Thr Cys Asn Val Ala His Pro Ala Ser
        275                 280                 285
Ser Thr Lys Val Asp Lys Lys Ile Val Pro Arg Asp Cys Gly Cys Lys
    290                 295                 300
Pro Cys Ile Cys Thr Val Pro Glu Val Ser Ser Val Phe Ile Phe Pro
305                 310                 315                 320
```

```
Pro Lys Pro Lys Asp Val Leu Thr Ile Thr Leu Thr Pro Lys Val Thr
                325                 330                 335

Cys Val Val Asp Ile Ser Lys Asp Asp Pro Glu Val Gln Phe Ser
        340                 345                 350

Trp Phe Val Asp Asp Val Glu Val His Thr Ala Gln Thr Gln Pro Arg
            355                 360                 365

Glu Glu Gln Phe Asn Ser Thr Phe Arg Ser Val Ser Glu Leu Pro Ile
370                 375                 380

Met His Gln Asp Trp Leu Asn Gly Lys Glu Phe Lys Cys Arg Val Asn
385                 390                 395                 400

Ser Ala Ala Phe Pro Ala Pro Ile Glu Lys Thr Ile Ser Lys Thr Lys
                405                 410                 415

Gly Arg Pro Lys Ala Pro Gln Val Tyr Thr Ile Pro Pro Lys Glu
                420                 425                 430

Gln Met Ala Lys Asp Lys Val Ser Leu Thr Cys Met Ile Thr Asp Phe
                435                 440                 445

Phe Pro Glu Asp Ile Thr Val Glu Trp Gln Trp Asn Gly Gln Pro Ala
            450                 455                 460

Glu Asn Tyr Lys Asn Thr Gln Pro Ile Met Asp Thr Asp Gly Ser Tyr
465                 470                 475                 480

Phe Val Tyr Ser Lys Leu Asn Val Gln Lys Ser Asn Trp Glu Ala Gly
                485                 490                 495

Asn Thr Phe Thr Cys Ser Val Leu His Glu Gly Leu His Asn His His
                500                 505                 510

Thr Glu Lys Ser Leu Ser His Ser Pro Gly Lys
                515                 520

<210> SEQ ID NO 4
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 4

Met Tyr Arg Met Gln Leu Leu Ser Cys Ile Ala Leu Ser Leu Ala Leu
1               5                   10                  15

Val Thr Asn Ser Asn Gln Cys Pro Glu His Ser Gln Leu Thr Ala Leu
                20                  25                  30

Gly Met Asp Asp Thr Glu Thr Pro Glu Pro His Leu Gly Leu Trp Tyr
            35                  40                  45

Phe Ile Ala Gly Ala Ala Pro Thr Thr Glu Glu Leu Ala Thr Phe Asp
        50                  55                  60

Pro Val Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
                85                  90                  95

Pro Arg Lys Trp Thr Tyr Arg Leu Thr Glu Gly Lys Gly Asn Met Glu
                100                 105                 110

Leu Arg Thr Glu Gly Arg Pro Asp Met Lys Thr Asp Leu Phe Ser Ser
            115                 120                 125

Ser Cys Pro Gly Gly Ile Met Leu Lys Glu Thr Gly Gln Gly Tyr Gln
        130                 135                 140

Arg Phe Leu Leu Tyr Asn Arg Ser Pro His Pro Pro Glu Lys Cys Val
145                 150                 155                 160
```

```
Glu Glu Phe Lys Ser Leu Thr Ser Cys Leu Asp Phe Lys Ala Phe Leu
                165                 170                 175

Val Thr Pro Arg Asn Gln Glu Ala Cys Pro Leu Ser Ser Lys Trp Ala
            180                 185                 190

Ser Thr Lys Gly Pro Ser Val Phe Pro Leu Ala Pro Ser Ser Lys Ser
        195                 200                 205

Thr Ser Gly Gly Thr Ala Ala Leu Gly Cys Leu Val Lys Asp Tyr Phe
210                 215                 220

Pro Glu Pro Val Thr Val Ser Trp Asn Ser Gly Ala Leu Thr Ser Gly
225                 230                 235                 240

Val His Thr Phe Pro Ala Val Leu Gln Ser Ser Gly Leu Tyr Ser Leu
                245                 250                 255

Ser Ser Val Val Thr Val Pro Ser Ser Ser Leu Gly Thr Gln Thr Tyr
            260                 265                 270

Ile Cys Asn Val Asn His Lys Pro Ser Asn Thr Lys Val Asp Lys Lys
        275                 280                 285

Val Glu Pro Lys Ser Cys Asp Lys Thr His Thr Cys Pro Pro Cys Pro
290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
            340                 345                 350

Val Asp Gly Val Glu Val His Asn Ala Lys Thr Lys Pro Arg Glu Glu
        355                 360                 365

Gln Tyr Asn Ser Thr Tyr Arg Val Val Ser Val Leu Thr Val Leu His
370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Glu Glu Met
            420                 425                 430

Thr Lys Asn Gln Val Ser Leu Thr Cys Leu Val Lys Gly Phe Tyr Pro
        435                 440                 445

Ser Asp Ile Ala Val Glu Trp Glu Ser Asn Gly Gln Pro Glu Asn Asn
450                 455                 460

Tyr Lys Thr Thr Pro Pro Val Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
            500                 505                 510

Lys Ser Leu Ser Leu Ser Pro Gly Lys
        515                 520

<210> SEQ ID NO 5
<211> LENGTH: 168
<212> TYPE: PRT
<213> ORGANISM: Artificial Sequence
<220> FEATURE:
<223> OTHER INFORMATION: Synthetic polypeptide
```

<400> SEQUENCE: 5

Tyr Gln Cys Pro Glu His Ser Gln Leu Thr Thr Leu Gly Val Asp Gly
1               5                   10                  15

Lys Glu Phe Pro Glu Val His Leu Gly Gln Trp Tyr Phe Ile Ala Gly
            20                  25                  30

Ala Ala Pro Thr Lys Glu Glu Leu Ala Thr Phe Asp Pro Val Asp Asn
        35                  40                  45

Ile Val Phe Asn Met Ala Ala Gly Ser Ala Pro Met Gln Leu His Leu
50                  55                  60

Arg Ala Thr Ile Arg Met Lys Asp Gly Leu Cys Val Pro Arg Lys Trp
65                  70                  75                  80

Ile Tyr His Leu Thr Glu Gly Ser Thr Asp Leu Arg Thr Glu Gly Arg
                85                  90                  95

Pro Asp Met Lys Thr Glu Leu Phe Ser Ser Cys Pro Gly Gly Ile
            100                 105                 110

Met Leu Asn Glu Thr Gly Gln Gly Tyr Gln Arg Phe Leu Leu Tyr Asn
            115                 120                 125

Arg Ser Pro His Pro Glu Lys Cys Val Glu Glu Phe Lys Ser Leu
130                 135                 140

Thr Ser Cys Leu Asp Ser Lys Ala Phe Leu Leu Thr Pro Arg Asn Gln
145                 150                 155                 160

Glu Ala Cys Glu Leu Ser Asn Asn
                165

<210> SEQ ID NO 6
<211> LENGTH: 170
<212> TYPE: PRT
<213> ORGANISM: Artificial Sequence
<220> FEATURE:
<223> OTHER INFORMATION: Synthetic polypeptide

<400> SEQUENCE: 6

Asn Gln Cys Pro Glu His Ser Gln Leu Thr Ala Leu Gly Met Asp Asp
1               5                   10                  15

Thr Glu Thr Pro Glu Pro His Leu Gly Leu Trp Tyr Phe Ile Ala Gly
            20                  25                  30

Ala Ala Pro Thr Thr Glu Glu Leu Ala Thr Phe Asp Pro Val Asp Asn
        35                  40                  45

Ile Val Phe Asn Met Ala Ala Gly Ser Ala Pro Arg Gln Leu Gln Leu
50                  55                  60

Arg Ala Thr Ile Arg Thr Lys Ser Gly Val Cys Val Pro Arg Lys Trp
65                  70                  75                  80

Thr Tyr Arg Leu Thr Glu Gly Lys Gly Asn Met Glu Leu Arg Thr Glu
                85                  90                  95

Gly Arg Pro Asp Met Lys Thr Asp Leu Phe Ser Ser Cys Pro Gly
            100                 105                 110

Gly Ile Met Leu Lys Glu Thr Gly Gln Gly Tyr Gln Arg Phe Leu Leu
            115                 120                 125

Tyr Asn Arg Ser Pro His Pro Pro Glu Lys Cys Val Glu Glu Phe Lys
130                 135                 140

Ser Leu Thr Ser Cys Leu Asp Phe Lys Ala Phe Leu Val Thr Pro Arg
145                 150                 155                 160

Asn Gln Glu Ala Cys Pro Leu Ser Ser Lys
                165                 170

<210> SEQ ID NO 7
<211> LENGTH: 331
<212> TYPE: PRT
<213> ORGANISM: Artificial Sequence
<220> FEATURE:
<223> OTHER INFORMATION: Synthetic polypeptide

<400> SEQUENCE: 7

```
Trp Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

<210> SEQ ID NO 8
<211> LENGTH: 331
<212> TYPE: PRT
<213> ORGANISM: Artificial Sequence
<220> FEATURE:

<223> OTHER INFORMATION: Synthetic polypeptide

<400> SEQUENCE: 8

```
Trp Ile Ser Ser Ala Ser Ala Lys Thr Thr Pro Pro Ser Val Tyr
1               5                   10                  15

Pro Leu Ala Pro Gly Ser Ala Ala Gln Thr Asn Ser Met Val Thr Leu
            20                  25                  30

Gly Cys Leu Val Lys Gly Tyr Phe Pro Glu Pro Val Thr Val Thr Trp
            35                  40                  45

Asn Ser Gly Ser Leu Ser Ser Gly Val His Thr Phe Pro Ala Val Leu
 50                  55                  60

Gln Ser Asp Leu Tyr Thr Leu Ser Ser Val Thr Val Pro Ser Ser
 65                  70                  75                  80

Thr Trp Pro Ser Glu Thr Val Thr Cys Asn Val Ala His Pro Ala Ser
                85                  90                  95

Ser Thr Lys Val Asp Lys Lys Ile Val Pro Arg Asp Cys Gly Cys Lys
            100                 105                 110

Pro Cys Ile Cys Thr Val Pro Glu Val Ser Ser Val Phe Ile Phe Pro
            115                 120                 125

Pro Lys Pro Lys Asp Val Leu Thr Ile Thr Leu Thr Pro Lys Val Thr
            130                 135                 140

Cys Val Val Val Asp Ile Ser Lys Asp Pro Glu Val Gln Phe Ser
145                 150                 155                 160

Trp Phe Val Asp Asp Val Glu Val His Thr Ala Gln Thr Gln Pro Arg
                165                 170                 175

Glu Glu Gln Phe Asn Ser Thr Phe Arg Ser Val Ser Glu Leu Pro Ile
            180                 185                 190

Met His Gln Asp Trp Leu Asn Gly Lys Glu Phe Lys Cys Arg Val Asn
        195                 200                 205

Ser Ala Ala Phe Pro Ala Pro Ile Glu Lys Thr Ile Ser Lys Thr Lys
210                 215                 220

Gly Arg Pro Lys Ala Pro Gln Val Tyr Thr Ile Pro Pro Lys Glu
225                 230                 235                 240

Gln Met Ala Lys Asp Lys Val Ser Leu Thr Cys Met Ile Thr Asp Phe
                245                 250                 255

Phe Pro Glu Asp Ile Thr Val Glu Trp Gln Trp Asn Gly Gln Pro Ala
            260                 265                 270

Glu Asn Tyr Lys Asn Thr Gln Pro Ile Met Asp Thr Asp Gly Ser Tyr
        275                 280                 285

Phe Val Tyr Ser Lys Leu Asn Val Gln Lys Ser Asn Trp Glu Ala Gly
    290                 295                 300

Asn Thr Phe Thr Cys Ser Val Leu His Glu Gly Leu His Asn His His
305                 310                 315                 320

Thr Glu Lys Ser Leu Ser His Ser Pro Gly Lys
                325                 330
```

<210> SEQ ID NO 9
<211> LENGTH: 527
<212> TYPE: PRT
<213> ORGANISM: Artificial Sequence
<220> FEATURE:
<223> OTHER INFORMATION: Synthetic polypeptide

<400> SEQUENCE: 9

```
Met Tyr Arg Met Gln Leu Leu Ser Cys Ile Ala Leu Ser Leu Ala Leu
1               5                   10                  15
```

-continued

Val Thr Asn Ser Asn Gln Cys Pro Glu His Ser Gln Leu Thr Ala Leu
            20                  25                  30

Gly Met Asp Asp Thr Glu Thr Pro Glu Pro His Leu Gly Leu Trp Tyr
        35                  40                  45

Phe Ile Ala Gly Ala Ala Pro Thr Thr Glu Glu Leu Ala Thr Phe Asp
50                  55                  60

Pro Val Asp Asn Ile Val Phe Asn Met Ala Ala Gly Ser Ala Pro Arg
65                  70                  75                  80

Gln Leu Gln Leu Arg Ala Thr Ile Arg Thr Lys Ser Gly Val Cys Val
                85                  90                  95

Pro Arg Lys Trp Thr Tyr Arg Leu Thr Glu Gly Lys Gly Asn Met Glu
            100                 105                 110

Leu Arg Thr Glu Gly Arg Pro Asp Met Lys Thr Asp Leu Phe Ser Ser
        115                 120                 125

Ser Cys Pro Gly Gly Ile Met Leu Lys Glu Thr Gly Gln Gly Tyr Gln
130                 135                 140

Arg Phe Leu Leu Tyr Asn Arg Ser Pro His Pro Glu Lys Cys Val
145                 150                 155                 160

Glu Glu Phe Lys Ser Leu Thr Ser Cys Leu Asp Phe Lys Ala Phe Leu
            165                 170                 175

Val Thr Pro Arg Asn Gln Glu Ala Cys Pro Leu Ser Ser Lys Trp Ile
        180                 185                 190

Ser Ser Ala Ser Ser Ala Lys Thr Thr Pro Pro Ser Val Tyr Pro Leu
195                 200                 205

Ala Pro Gly Ser Ala Ala Gln Thr Asn Ser Met Val Thr Leu Gly Cys
            210                 215                 220

Leu Val Lys Gly Tyr Phe Pro Glu Pro Val Thr Val Thr Trp Asn Ser
225                 230                 235                 240

Gly Ser Leu Ser Ser Gly Val His Thr Phe Pro Ala Val Leu Gln Ser
            245                 250                 255

Asp Leu Tyr Thr Leu Ser Ser Ser Val Thr Val Pro Ser Ser Thr Trp
        260                 265                 270

Pro Ser Glu Thr Val Thr Cys Asn Val Ala His Pro Ala Ser Ser Thr
    275                 280                 285

Lys Val Asp Lys Lys Ile Val Pro Arg Asp Cys Gly Cys Lys Pro Cys
290                 295                 300

Ile Cys Thr Val Pro Glu Val Ser Ser Val Phe Ile Phe Pro Pro Lys
305                 310                 315                 320

Pro Lys Asp Val Leu Thr Ile Thr Leu Thr Pro Lys Val Thr Cys Val
            325                 330                 335

Val Val Asp Ile Ser Lys Asp Asp Pro Glu Val Gln Phe Ser Trp Phe
        340                 345                 350

Val Asp Asp Val Glu Val His Thr Ala Gln Thr Gln Pro Arg Glu Glu
    355                 360                 365

Gln Phe Asn Ser Thr Phe Arg Ser Val Ser Glu Leu Pro Ile Met His
370                 375                 380

Gln Asp Trp Leu Asn Gly Lys Glu Phe Lys Cys Arg Val Asn Ser Ala
385                 390                 395                 400

Ala Phe Pro Ala Pro Ile Glu Lys Thr Ile Ser Lys Thr Lys Gly Arg
            405                 410                 415

Pro Lys Ala Pro Gln Val Tyr Thr Ile Pro Pro Pro Lys Glu Gln Met
        420                 425                 430

```
Ala Lys Asp Lys Val Ser Leu Thr Cys Met Ile Thr Asp Phe Phe Pro
            435                 440                 445

Glu Asp Ile Thr Val Glu Trp Gln Trp Asn Gly Gln Pro Ala Glu Asn
    450                 455                 460

Tyr Lys Asn Thr Gln Pro Ile Met Asp Thr Asp Gly Ser Tyr Phe Val
465                 470                 475                 480

Tyr Ser Lys Leu Asn Val Gln Lys Ser Asn Trp Glu Ala Gly Asn Thr
                485                 490                 495

Phe Thr Cys Ser Val Leu His Glu Gly Leu His Asn His His Thr Glu
            500                 505                 510

Lys Ser Leu Ser His Ser Pro Gly Lys His His His His His His
            515                 520                 525

<210> SEQ ID NO 10
<211> LENGTH: 1566
<212> TYPE: DNA
<213> ORGANISM: Artificial Sequence
<220> FEATURE:
<223> OTHER INFORMATION: Synthetic polynucleotide

<400> SEQUENCE: 10
atgtacagga tgcaactcct gtcttgcatt gcactaagtc ttgcacttgt cacgaattcg     60
aatcagtgcc ctgagcacag tcaactaact gcgctgggaa tggacgacac agagacccca    120
gagccccacc tgggcctgtg gtactttatt gcgggagcag cccccaccac ggaagagttg    180
gcaacttttg atccggtgga caatattgtc ttcaacatgg ctgccggctc tgccccaagg    240
cagctccagc ttcgtgctac catccgcacg aaaagtgggg tctgtgtgcc ccggaagtgg    300
acataccgat tgactgaagg gaaaggaaac atggaactca gaactgaagg cgcccagac    360 atgaaaacag acctgttctc cagctcgtgc ccaggaggaa tcatgctgaa agagacgggc    420
cagggctacc agcgctttct cctctacaat cggtcaccac accctccaga gaagtgtgtg    480
gaggaattca gtctctgac ctcttgcttg gacttcaaag ccttcttagt gactcccagg    540
aatcaagagg cctgcccgct gtccagcaag tggatctcga gtgctagcag cgctaaaacg    600
acacccccat ctgtctatcc actggcccct ggatctgctg cccaaactaa ctccatggtg    660
accctgggat gcctggtcaa gggctatttc cctgagccag tgacagtgac ctggaactct    720
ggatccctgt ccagcggtgt gcacaccttc ccagctgtcc tgcagtctga cctctacact    780
ctgagcagct cagtgactgt cccctccagc acctggccca gcgagaccgt cacctgcaac    840
gttgcccacc cggccagcag caccaaggtg gacaagaaaa ttgtgcccag ggattgtggt    900
tgtaagcctt gcatatgtac agtcccagaa gtatcatctg tcttcatctt cccccccaaag    960 cccaaggatg tgctcaccat tactctgact cctaaggtca cgtgtgttgt ggtagacatc   1020
agcaaggatg atcccgaggt ccagttcagc tggtttgtag atgatgtgga ggtgcacaca   1080
gctcagacgc aaccccggga ggagcagttc aacagcactt tccgctcagt cagtgaactt   1140
cccatcatgc accaggactg gctcaatggc aaggagttca atgcagggt caacagtgca   1200 gctttccctg cccccatcga gaaaaccatc tccaaaacca aggcagacc gaaggctccg   1260 caggtgtaca ccattccacc tcccaaggag cagatggcca aggataaagt cagtctgacc   1320
tgcatgataa cagacttctt ccctgaagac attactgtgg agtggcagtg gaatgggcag   1380
ccagcggaga actacaagaa cactcagccc atcatggaca cagatggctc ttacttcgtc   1440
```

```
tacagcaagc tcaatgtgca gaagagcaac tgggaggcag gaaatacttt cacctgctct    1500
gtgttacatg agggcctgca caaccaccat actgagaaga gcctctccca ctctcctggt    1560
aaatga                                                               1566

<210> SEQ ID NO 11
<211> LENGTH: 1572
<212> TYPE: DNA
<213> ORGANISM: Artificial Sequence
<220> FEATURE:
<223> OTHER INFORMATION: Synthetic polynucleotide

<400> SEQUENCE: 11
atgtacagga tgcaactcct gtcttgcatt gcactaagtc ttgcacttgt cacgaattcg      60
atatctcgag tgtaccagtg ccctgagcac agtcaactga caactctggg cgtggatggg     120
aaggagttcc cagaggtcca cttgggccag tggtacttta tcgcaggggc agctcccacc     180
aaggaggagt tggcaacttt tgaccctgtg gacaacattg tcttcaatat ggctgctggc     240
tctgccccga tgcagctcca ccttcgtgct accatccgca tgaaagatgg gctctgtgtg     300
ccccggaaat ggatctacca cctgactgaa gggagcacag atctcagaac tgaaggccgc     360
cctgacatga agactgagct cttttccagc tcatgcccag gtggaatcat gctgaatgag     420
acaggccagg gttaccagcg cttttctcctc tacaatcgct caccacatcc tcccgaaaag    480
tgtgtggagg aattcaagtc cctgacttcc tgcctggact ccaaagcctt cttattgact     540
cctaggaatc aagaggcctg tgagctgtcc aataactggg ctagcaccaa gggcccatcg     600
gtcttccccc tggcaccctc ctccaagagc acctctgggg gcacagcggc cctgggctgc     660
ctggtcaagg actacttccc cgaaccggtg acggtgtcgt ggaactcagg cgccctgacc     720
agcggcgtgc acaccttccc ggctgtccta cagtcctcag gactctactc cctcagcagc     780
gtggtgaccg tgccctccag cagcttgggc acccagacct acatctgcaa cgtgaatcac     840
aagcccagca acaccaaggt ggacaagaaa gttgagccca atcttgtgac aaaaactcac     900
acatgcccac cgtgcccagc acctgaactc ctggggggac cgtcagtctt cctcttcccc     960
ccaaaaccca aggacaccct catgatctcc cggacccctg aggtcacatg cgtggtggtg    1020
gacgtgagcc acgaagaccc tgaggtcaag ttcaactggt acgtggacgg cgtggaggtg    1080
cataatgcca agacaaagcc gcgggaggag cagtacaaca gcacgtaccg tgtggtcagc    1140
gtcctcaccg tcctgcacca ggactggctg aatggcaagg agtacaagtg caaggtctcc    1200
aacaaagccc tcccagcccc catcgagaaa accatctccc aagccaaagg gcagccccga    1260
gaaccacagg tgtacaccct gcccccatcc cgggaggaga tgaccaagaa ccaggtcagc    1320
ctgacctgcc tggtcaaagg cttctatccc agcgacatcg ccgtggagtg ggagagcaat    1380
gggcagccgg agaacaacta caagaccacg cctcccgtgc tggactccga cggctccttc    1440
ttcctctaca gcaagctcac cgtggacaag agcaggtggc agcaggggaa cgtcttctca    1500
tgctccgtga tgcatgaggc tctgcacaac cactacacgc agaagagcct ctccctgtct    1560
ccgggtaaat ga                                                        1572

<210> SEQ ID NO 12
<211> LENGTH: 1572
<212> TYPE: DNA
<213> ORGANISM: Artificial Sequence
<220> FEATURE:
<223> OTHER INFORMATION: Synthetic polynucleotide
```

<400> SEQUENCE: 12

```
atgtacagga tgcaactcct gtcttgcatt gcactaagtc ttgcacttgt cacgaattcg      60
atatctcgag tgtaccagtg ccctgagcac agtcaactga caactctggg cgtggatggg     120
aaggagttcc cagaggtcca cttgggccag tggtacttta tcgcagggc agctcccacc      180
aaggaggagt tggcaacttt tgaccctgtg acaacattg tcttcaatat ggctgctggc      240
tctgccccga tgcagctcca ccttcgtgct accatccgca tgaaagatgg gctctgtgtg     300
ccccggaaat ggatctacca cctgactgaa gggagcacag atctcagaac tgaaggccgc     360
cctgacatga agactgagct cttttccagc tcatgcccag gtggaatcat gctgaatgag     420
acaggccagg gttaccagcg ctttctcctc tacaatcgct caccacatcc tcccgaaaag     480
tgtgtggagg aattcaagtc cctgacttcc tgcctggact ccaaagcctt cttattgact     540
cctaggaatc aagaggcctg tgagctgtcc aataactgga tctcgagtgc tagcagcgct     600
aaaacgacac ccccatctgt ctatccactg gcccctggat ctgctgccca aactaactcc     660
atggtgaccc tgggatgcct ggtcaagggc tatttccctg agccagtgac agtgacctgg     720
aactctggat ccctgtccag cggtgtgcac accttcccag ctgtcctgca gtctgacctc     780
tacactctga gcagctcagt gactgtcccc tccagcacct ggcccagcga gaccgtcacc     840
tgcaacgttg cccacccggc cagcagcacc aaggtggaca gaaaattgt gcccagggat      900
tgtggttgta agccttgcat atgtacagtc ccagaagtat catctgtctt catcttcccc     960
ccaaagccca aggatgtgct caccattact ctgactccta aggtcacgtg tgttgtggta    1020
gacatcagca aggatgatcc cgaggtccag ttcagctggt ttgtagatga tgtggaggtg    1080
cacacagctc agacgcaacc ccgggaggag cagttcaaca gcactttccg ctcagtcagt    1140
gaacttccca tcatgcacca ggactggctc aatggcaagg agttcaaatg cagggtcaac    1200
agtgcagctt tccctgcccc catcgagaaa accatctcca aaccaaagg cagaccgaag     1260
gctccgcagg tgtacaccat tccacctccc aaggagcaga tggccaagga taaagtcagt    1320
ctgacctgca tgataacaga cttcttccct gaagacatta ctgtggagtg cagtggaat     1380
gggcagccag cggagaacta caagaacact cagcccatca tggacacaga tggctcttac    1440
ttcgtctaca gcaagctcaa tgtgcagaag agcaactggg aggcaggaaa tactttcacc    1500
tgctctgtgt acatgagggg cctgcacaac accatactg agaagagcct ctcccactct    1560
cctggtaaat ga                                                        1572
```

<210> SEQ ID NO 13
<211> LENGTH: 1566
<212> TYPE: DNA
<213> ORGANISM: Artificial Sequence
<220> FEATURE:
<223> OTHER INFORMATION: Synthetic polynucleotide

<400> SEQUENCE: 13

```
atgtacagga tgcaactcct gtcttgcatt gcactaagtc ttgcacttgt cacgaattcg      60
aatcagtgcc ctgagcacag tcaactaact gcgctgggaa tggacgacac agagacccca    120
gagccccacc tgggcctgtg gtactttatt gcgggagcag cccccaccac ggaagagttg    180
gcaacttttg atccggtgga caatattgtc ttcaacatgg ctgccggctc tgccccaagg    240
cagctccagc ttcgtgctac catccgcacg aaaagtgggg tctgtgtgcc ccggaagtgg    300
acataccgat tgactgaagg gaaggaaac atggaactca gaactgaagg cgcccagac      360
atgaaaacag acctgttctc cagctcgtgc ccaggaggaa tcatgctgaa agagacgggc    420
```

```
cagggctacc agcgctttct cctctacaat cggtcaccac accctccaga gaagtgtgtg    480
gaggaattca agtctctgac ctcttgcttg gacttcaaag ccttcttagt gactcccagg    540
aatcaagagg cctgcccgct gtccagcaag tgggctagca ccaagggccc atcggtcttc    600
cccctggcac cctcctccaa gagcacctct ggggcacacg cggccctggg ctgcctggtc    660
aaggactact ccccgaaccc ggtgacggtg tcgtggaact caggcgccct gaccagcggc    720
gtgcacacct tcccggctgt cctacagtcc tcaggactct actccctcag cagcgtggtg    780
accgtgccct ccagcagctt gggcacccag acctacatct gcaacgtgaa tcacaagccc    840
agcaacacca aggtggacaa gaaagttgag cccaaatctt gtgacaaaac tcacacatgc    900
ccaccgtgcc cagcacctga actcctgggg ggaccgtcag tcttcctctt ccccccaaaa    960
cccaaggaca ccctcatgat ctcccggacc cctgaggtca catgcgtggt ggtggacgtg   1020
agccacgaag accctgaggt caagttcaac tggtacgtgg acggcgtgga ggtgcataat   1080
gccaagacaa agccgcggga ggagcagtac aacagcacgt accgtgtggt cagcgtcctc   1140
accgtcctgc accaggactg gctgaatggc aaggagtaca agtgcaaggt ctccaacaaa   1200
gccctcccag cccccatcga gaaaaccatc tccaaagcca agggcagccc cgagaaccca   1260
caggtgtaca ccctgccccc atcccgggag gagatgacca agaaccaggt cagcctgacc   1320
tgcctggtca aaggcttcta tcccagcgac atcgccgtgg agtgggagag caatgggcag   1380
ccggagaaca actacaagac cacgcctccc gtgctggact ccgacggctc cttcttcctc   1440
tacagcaagc tcaccgtgga caagagcagg tggcagcagg ggaacgtctt ctcatgctcc   1500
gtgatgcatg aggctctgca caaccactac acgcagaaga gcctctccct gtctccgggt   1560
aaatga                                                              1566

<210> SEQ ID NO 14
<211> LENGTH: 1584
<212> TYPE: DNA
<213> ORGANISM: Artificial Sequence
<220> FEATURE:
<223> OTHER INFORMATION: Synthetic polynucleotide

<400> SEQUENCE: 14
atgtacagga tgcaactcct gtcttgcatt gcactaagtc ttgcacttgt cacgaattcg     60
aatcagtgcc ctgagcacag tcaactaact gcgctgggaa tggacgacac agagacccca    120
gagccccacc tgggcctgtg gtactttatt gcgggagcag cccccaccac ggaagagttg    180
gcaacttttg atccggtgga caatattgtc ttcaacatgg ctgccggctc tgccccaagg    240
cagctccagc ttcgtgctac catccgcacg aaaagtgggg tctgtgtgcc ccggaagtgg    300
acataccgat tgactgaagg gaaaggaaac atggaactca gaactgaagg cgcccagac    360 atgaaaacag acctgttctc cagctcgtgc ccaggaggaa tcatgctgaa agagacgggc    420
cagggctacc agcgctttct cctctacaat cggtcaccac accctccaga gaagtgtgtg    480
gaggaattca agtctctgac ctcttgcttg gacttcaaag ccttcttagt gactcccagg    540
aatcaagagg cctgcccgct gtccagcaag tggatctcga gtgctagcag cgctaaaacg    600
acacccccat ctgtctatcc actggcccct ggatctgctg cccaaactaa ctccatggtg    660
accctgggat gcctggtcaa gggctatttc cctgagccag tgacagtgac ctggaactct    720
ggatccctgt ccagcggtgt gcacaccttc ccagctgtcc tgcagtctga cctctacact    780
ctgagcagct cagtgactgt cccctccagc acctggccca gcgagaccgt cacctgcaac    840
```

```
gttgcccacc cggccagcag caccaaggtg acaagaaaa ttgtgcccag ggattgtggt    900
tgtaagcctt gcatatgtac agtcccagaa gtatcatctg tcttcatctt ccccccaaag   960
cccaaggatg tgctcaccat tactctgact cctaaggtca cgtgtgttgt ggtagacatc  1020
agcaaggatg atcccgaggt ccagttcagc tggtttgtag atgatgtgga ggtgcacaca  1080
gctcagacgc aaccccggga ggagcagttc aacagcactt tccgctcagt cagtgaactt  1140
cccatcatgc accaggactg gctcaatggc aaggagttca atgcagggt caacagtgca   1200 gctttccctg cccccatcga aaaaccatc tccaaaacca aaggcagacc gaaggctccg   1260
caggtgtaca ccattccacc tcccaaggag cagatggcca aggataaagt cagtctgacc  1320
tgcatgataa cagacttctt ccctgaagac attactgtgg agtggcagtg aatgggcag   1380 ccagcggaga actacaagaa cactcagccc atcatggaca cagatggctc ttacttcgtc  1440
tacagcaagc tcaatgtgca aagagcaac tgggaggcag aaatactttt cacctgctct   1500
gtgttacatg agggcctgca caaccaccat actgagaaga gcctctccca ctctcctggt  1560
aaacatcacc atcaccatca ctga                                         1584
```

<210> SEQ ID NO 15
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 15

Met Tyr Arg Met Gln Leu Leu Ser Cys Ile Ala Leu Ser Leu Ala Leu
1               5                   10                  15

Val Thr Asn Ser
            20

<210> SEQ ID NO 16
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 16

Met Asp Trp Thr Trp Ile Leu Phe Leu Val Ala Ala Thr Arg Val
1               5                   10                  15

His Ser

<210> SEQ ID NO 17
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 17

Met Glu Thr Pro Ala Gln Leu Leu Phe Leu Leu Leu Trp Leu Pro
1               5                   10                  15

Asp Thr Thr Gly
            20

<210> SEQ ID NO 18
<211> LENGTH: 16
<212> TYPE: PRT
<213> ORGANISM: Artificial Sequence
<220> FEATURE:

<223> OTHER INFORMATION: Synthetic polypeptide

<400> SEQUENCE: 18

Ser Gly Ser Glu Thr Pro Gly Thr Ser Glu Ser Ala Thr Pro Glu Ser
1               5                   10                  15

<210> SEQ ID NO 19
<211> LENGTH: 120
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(120)
<223> OTHER INFORMATION: May be absent

<400> SEQUENCE: 19

Ser Gly Gly Ser Ser Gly Gly Ser Ser Gly Gly Ser Ser Gly Gly Ser
1               5                   10                  15

Ser Gly Gly Ser Ser Gly Gly Ser Ser Gly Gly Ser Ser Gly Gly Ser
                20                  25                  30

Ser Gly Gly Ser Ser Gly Gly Ser Ser Gly Gly Ser Ser Gly Gly Ser
            35                  40                  45

Ser Gly Gly Ser Ser Gly Gly Ser Ser Gly Gly Ser Ser Gly Gly Ser
        50                  55                  60

Ser Gly Gly Ser Ser Gly Gly Ser Ser Gly Gly Ser Ser Gly Gly Ser
65                  70                  75                  80

Ser Gly Gly Ser Ser Gly Gly Ser Ser Gly Gly Ser Ser Gly Gly Ser
                85                  90                  95

Ser Gly Gly Ser Ser Gly Gly Ser Ser Gly Gly Ser Ser Gly Gly Ser
            100                 105                 110

Ser Gly Gly Ser Ser Gly Gly Ser
        115                 120

<210> SEQ ID NO 20
<211> LENGTH: 120
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (5)..(120)
<223> OTHER INFORMATION: May be absent

<400> SEQUENCE: 20

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser Gly Gly Gly Ser Gly Gly Gly Ser
            35                  40                  45

Gly Gly Gly Ser Gly Gly Gly Ser Gly Gly Gly Ser Gly Gly Gly Ser
        50                  55                  60

Gly Gly Gly Ser Gly Gly Gly Ser Gly Gly Gly Ser Gly Gly Gly Ser
65                  70                  75                  80

Gly Gly Gly Ser Gly Gly Gly Ser Gly Gly Gly Ser Gly Gly Gly Ser
                85                  90                  95

Gly Gly Gly Ser Gly Gly Gly Ser Gly Gly Gly Ser Gly Gly Gly Ser
            100                 105                 110

Gly Gly Gly Ser Gly Gly Gly Ser
        115             120

<210> SEQ ID NO 21
<211> LENGTH: 150
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(150)
<223> OTHER INFORMATION: May be absent

<400> SEQUENCE: 21

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser Gly Gly
                20                  25                  30

Gly Gly Ser Gly Gly Gly Ser Gly Gly Gly Ser Gly Gly Gly
            35                  40                  45

Gly Ser Gly Gly Gly Ser Gly Gly Gly Ser Gly Gly Gly Gly
        50                  55                  60

Ser Gly Gly Gly Ser Gly Gly Gly Ser Gly Gly Gly Gly Ser
65                  70                  75                  80

Gly Gly Gly Gly Ser Gly Gly Gly Ser Gly Gly Gly Ser Gly
                85                  90                  95

Gly Gly Gly Ser Gly Gly Gly Ser Gly Gly Gly Ser Gly Gly
                100                 105                 110

Gly Gly Ser Gly Gly Gly Ser Gly Gly Gly Ser Gly Gly Gly
            115                 120                 125

Gly Ser Gly Gly Gly Ser Gly Gly Gly Ser Gly Gly Gly Gly
        130                 135                 140

Ser Gly Gly Gly Gly Ser
145                 150

<210> SEQ ID NO 22
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(30)
<223> OTHER INFORMATION: May be absent

<400> SEQUENCE: 22

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
                20                  25                  30

<210> SEQ ID NO 23
<211> LENGTH: 150
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(150)
<223> OTHER INFORMATION: May be absent

<400> SEQUENCE: 23

Glu Ala Ala Ala Lys Glu Ala Ala Lys Glu Ala Ala Lys Glu
1               5                   10                  15

Ala Ala Ala Lys Glu Ala Ala Lys Glu Ala Ala Lys Glu Ala
            20                  25                  30

Ala Ala Lys Glu Ala Ala Lys Glu Ala Ala Lys Glu Ala Ala
        35                  40                  45

Ala Lys Glu Ala Ala Lys Glu Ala Ala Lys Glu Ala Ala Ala
    50                  55                  60

Lys Glu Ala Ala Lys Glu Ala Ala Lys Glu Ala Ala Ala Lys
65                  70                  75                  80

Glu Ala Ala Lys Glu Ala Ala Lys Glu Ala Ala Lys Glu
                85                  90                  95

Ala Ala Ala Lys Glu Ala Ala Lys Glu Ala Ala Lys Glu Ala
            100                 105                 110

Ala Ala Lys Glu Ala Ala Lys Glu Ala Ala Lys Glu Ala Ala
        115                 120                 125

Ala Lys Glu Ala Ala Lys Glu Ala Ala Lys Glu Ala Ala Ala
    130                 135                 140

Lys Glu Ala Ala Ala Lys
145                 150

<210> SEQ ID NO 24
<211> LENGTH: 90
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (4)..(90)
<223> OTHER INFORMATION: May be absent

<400> SEQUENCE: 24

Gly Gly Ser Gly Gly Ser Gly Gly Ser Gly Gly Ser Gly
1               5                   10                  15

Gly Ser Gly Gly Ser Gly Gly Ser Gly Gly Ser Gly Gly
            20                  25                  30

Ser Gly Gly Ser Gly Gly Ser Gly Gly Ser Gly Gly Ser
        35                  40                  45

Gly Gly Ser Gly Gly Ser Gly Gly Ser Gly Gly Ser Gly
    50                  55                  60

Gly Ser Gly Gly Ser Gly Gly Ser Gly Gly Ser Gly Gly
65                  70                  75                  80

Ser Gly Gly Ser Gly Gly Ser Gly Gly Ser
            85                  90

<210> SEQ ID NO 25
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 25

Ser Gly Gly Ser
1

```
<210> SEQ ID NO 26
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 26

Ser Gly Gly Ser Ser Gly Ser Glu Thr Pro Gly Thr Ser Glu Ser Ala
1               5                   10                  15

Thr Pro Glu Ser Ser Gly Gly Ser
            20

<210> SEQ ID NO 27
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 27

Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly Ser
            20                  25                  30

<210> SEQ ID NO 28
<211> LENGTH: 104
<212> TYPE: PRT
<213> ORGANISM: Artificial Sequence
<220> FEATURE:
<223> OTHER INFORMATION: Synthetic polypeptide

<400> SEQUENCE: 28

Gly Gly Ser Gly Gly Ser Pro Gly Ser Pro Ala Gly Ser Pro Thr Ser
1               5                   10                  15

Thr Glu Glu Gly Thr Ser Glu Ser Ala Thr Pro Glu Ser Gly Pro Gly
            20                  25                  30

Thr Ser Thr Glu Pro Ser Glu Gly Ser Ala Pro Gly Ser Pro Ala Gly
        35                  40                  45

Ser Pro Thr Ser Thr Glu Glu Gly Thr Ser Thr Glu Pro Ser Glu Gly
    50                  55                  60

Ser Ala Pro Gly Thr Ser Thr Glu Pro Ser Glu Gly Ser Ala Pro Gly
65                  70                  75                  80

Thr Ser Glu Ser Ala Thr Pro Glu Ser Gly Pro Gly Ser Glu Pro Ala
                85                  90                  95

Thr Ser Gly Gly Ser Gly Gly Ser
            100
```

ApoM-Fc FUSION PROTEINS FOR TREATING LUNG DISEASES

RELATED APPLICATION

This application is a national stage filing under 35 U.S.C. § 371 of International Patent Application Serial No. PCT/US2019/055831, filed Oct. 11, 2019, which claims the benefit under 35 U.S.C. § 119 (e) to U.S. Provisional Application No. 62/744,903, filed Oct. 12, 2018, and entitled "APOM-FC FUSION PROTEINS FOR TREATING LUNG DISEASES," each of which is incorporated herein by reference in its entirety.

GOVERNMENT SUPPORT

This invention was made with government support under grant numbers HL089934, HL007734, and HL135821 awarded by the National Institutes of Health. The government has certain rights in the invention.

The instant application contains a Sequence Listing which has been submitted in ASCII format via EFS-Web and is hereby incorporated by reference in its entirety. Said ASCII copy, created on Apr. 12, 2021, is named C123370153US01-SEQ-ZJG.txt, and is 53,049 bytes in size.

BACKGROUND

Apolipoprotein M (ApoM) binds to a lipid mediator sphingosine-1-phosphate (S1P) and chaperones S1P to activate cell surface G protein-coupled receptors (S1P receptors) to induce cellular responses. ApoM/S1P complex is involved in both acute and chronic disease conditions. Abnormal levels and/or activities of ApoM/S1P complex are observed in various diseases.

SUMMARY

Provided herein are methods of treating lung diseases using fusion proteins comprising ApoM (e.g., human or murine ApoM) fused to a constant region (Fc) of a immunoglobulin G (IgG, e.g., human IgG or murine IgG), referred to herein as the "ApoM-Fc fusion protein." The fusion protein is shown herein to increase lung regeneration and growth, and/or to restore lung architecture. The fusion protein may be administered to a subject in need of treatment of a lung disease at different stages, e.g., in uterus before the subject is born, within 1 hour or several hours of birth, within days or months of birth, or years after birth (e.g., in adulthood). Lung diseases that may be treated using the fusion protein described herein in include bronchopulmonary dysplasia (BPD), chronic obstructive pulmonary disease (COPD), congenital diaphragmatic hernia (CDH), pulmonary hypertension, pulmonary hypoplasia, pulmonary fibrosis or emphysema.

Accordingly, some aspects of the present disclosure provide methods of treating a lung disease, the method comprising administering to a subject in need thereof a therapeutically effective amount of a fusion protein comprising an apolipoprotein M (ApoM) fused to a constant region (Fc) of an immunoglobulin (IgG). In some embodiments, the fusion protein further comprises a signal peptide fused to the ApoM. In some embodiments, the IgG is IgG1.

In some embodiments, the ApoM is fused at the N-terminus of the Fc. In some embodiments, the ApoM is human ApoM or murine ApoM. In some embodiments, the Fc is human Fc or murine Fc. In some embodiments, the ApoM is human ApoM, and the Fc is human Fc. In some embodiments, the ApoM is murine ApoM, and the Fc is murine Fc. In some embodiments, the ApoM is human ApoM, and the Fc is murine Fc. In some embodiments, the ApoM is murine ApoM, and the Fc is human Fc.

In some embodiments, the ApoM comprises an amino acid sequence that is at least 70%, at least 80%, at least 90%, at least 95%, or at least 99% identical to SEQ ID NO: 5 or SEQ ID NO: 6. In some embodiments, the ApoM comprises the amino acid sequence of SEQ ID NO: 5 or SEQ ID NO: 6. In some embodiments, the ApoM consists of the amino acid sequence of SEQ ID NO: 5 or SEQ ID NO: 6.

In some embodiments, the Fc comprises an amino acid sequence that is at least 70%, at least 80%, at least 90%, at least 95%, at least 99%, or at least 99.5% identical to SEQ ID NO: 7 or SEQ ID NO: 8. In some embodiments, the Fc comprises the amino acid sequence of SEQ ID NO: 7 or SEQ ID NO: 8. In some embodiments, the Fc consists of the amino acid sequence of SEQ ID NO:7 or SEQ ID NO: 8.

In some embodiments, the fusion protein comprises an amino acid sequence that is at least 70%, at least 80%, at least 90%, at least 95%, or at least 99% identical to any one of SEQ ID NOs: 1-4 and 9. In some embodiments, the fusion protein comprises the amino acid sequence of any one of SEQ ID NO: 1-4 and 9. In some embodiments, the fusion protein consists of the amino acid sequence any one of SEQ ID NO: 1-4 and 9.

In some embodiments, the fusion protein is cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combinations thereof. In some embodiments, the fusion protein is conjugated to a polymer.

In some embodiments, the fusion protein comprises a chemical modification.

In some embodiments, the fusion protein activates a S1P receptor. In some embodiments, the S1P receptor is S1P1.

In some embodiments, the fusion protein is administered intravenously, intranasally, intratracheally, intramuscularly, or by inhalation. In some embodiments, the fusion protein is administered by inhalation using a mechanical device.

In some embodiments, the lung disease is bronchopulmonary dysplasia (BPD), chronic obstructive pulmonary disease (COPD), congenital diaphragmatic hernia (CDH), pulmonary hypertension, pulmonary hypoplasia, pulmonary fibrosis, emphysema, or asthma.

In some embodiments, the subject is human. In some embodiments, the fusion protein is administered to the human subject in utero. In some embodiments, the fusion protein is administered within one hour after birth. In some embodiments, the fusion protein is administered within one day after birth. In some embodiments, the fusion protein is administered within one week after birth. In some embodiments, the fusion protein is administered within one month after birth. In some embodiments, the fusion protein is administered within one year after birth. In some embodiments, the fusion protein is administered when the human subject is an adult.

In some embodiments, the subject is a rodent. In some embodiments, the rodent is a mouse or a rat.

In some embodiments, the fusion protein increases lung regeneration and growth.

Other aspects of the present disclosure provide fusion proteins comprising an apolipoprotein M (ApoM) fused to a constant region (Fc) of an immunoglobulin (IgG) for use in treating lung disease.

Further provided herein are methods of treating Bronchopulmonary Dysplasia (BPD), the method comprising administering to a human subject in need thereof a therapeutically effective amount of a fusion protein comprising an apolipoprotein M (ApoM) fused to a constant region (Fc) of an immunoglobulin G (IgG).

In some embodiments, the human subject was born prematurely. In some embodiments, the human subject was exposed to hyperoxia as a newborn.

In some embodiments, the fusion protein is administered to the human subject in utero. In some embodiments, the fusion protein is administered within one hour after birth. In some embodiments, the fusion protein is administered within one day after birth. In some embodiments, the fusion protein is administered within one week after birth. In some embodiments, the fusion protein is administered within one month after birth. In some embodiments, the fusion protein is administered within one year after birth. In some embodiments, the fusion protein is administered when the human subject is an adult.

In some embodiments, the fusion protein restores lung architecture.

Other aspects of the present disclosure provide methods of treating Congenital Diaphragmatic Hernia (CDH), the method comprising administering to a human subject in need thereof a therapeutically effective amount of a fusion protein comprising an apolipoprotein M (ApoM) fused to a constant region (Fc) of an immunoglobulin G (IgG).

In some embodiments, the fusion protein is administered to the human subject in utero. In some embodiments, the fusion protein is administered within one hour after birth. In some embodiments, the fusion protein is administered within one day after birth. In some embodiments, the fusion protein is administered within one week after birth. In some embodiments, the fusion protein is administered within one month after birth. In some embodiments, the fusion protein is administered within one year after birth. In some embodiments, the fusion protein is administered when the human subject is an adult.

In some embodiments, the fusion protein increases lung regeneration and growth. In some embodiments, the fusion protein restore lung development. In some embodiments, the human subject received surgical intervention.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIG. 1A) Histopathology sections of lungs from Newborn (P1) mice subjected to 10 days of either normoxia (Control; Panel 1 from left to right) or 90% Oxygen and treated with either Saline (Negative control; Panel 2 from left to right); ApoM-Fc-TM (4 mg/Kg; negative control; Panel 3 from left to right); or ApoM-Fc (4 mg/Kg; Panel 4 from left to right). (FIG. 1B) Quantitation of total alveoli from histopathology sections of lung described in FIG. 1A. Data represents the total intact alveoli/field for 5 separate microscopic fields from N=10 mice for each arm of the study. P=0.05 for mice treated with ApoM-Fc vs Saline control.

FIG. 2B), bronchial resistance (force required to distend lungs; FIG. 2C), and percent proliferating endothelial cells (FIG. 2D). Following lung evaluation, experimental lung samples were sectioned histologically and co-stained by immunohistochemistry for expression of the proliferation marker Ki-67 and the endothelial marker CD31. 5 microscopic fields were evaluated per slide and double staining cells were counted in a blinded manner. For these experiments n=4 and N=2. Graphs were generated using Prism software and statistical analysis employed a student's t-test.

DETAILED DESCRIPTION OF CERTAIN EMBODIMENTS

Figure 1A:
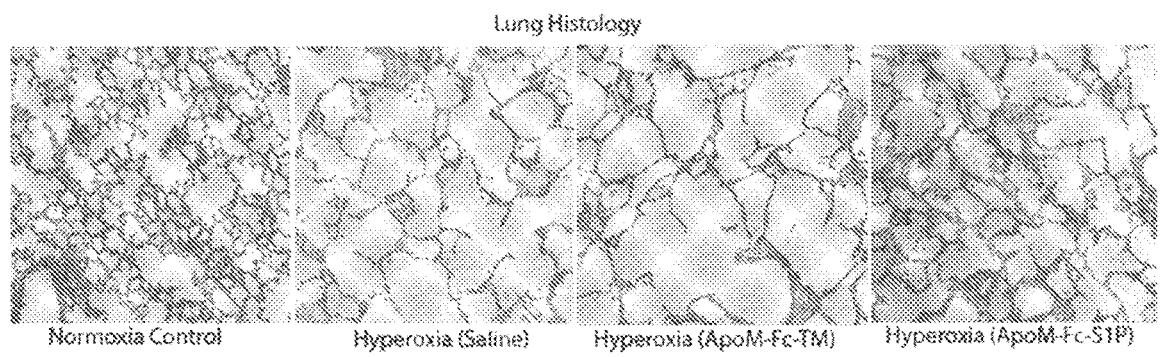
FIGS. 1A to 1B. ApoM-Fc preserves lung architecture in response to hyperoxia in the mouse model for bronchopulmonary dysplasia (BPD).

Sphingolipids and their metabolites, such as ceramide, sphingosine, and sphingosine-1-phosphate (S1P), are important bioregulators, capable of modulating acute lung injury in a variety of lung disorders.[12-14] S1P) plays an important role in vascular development and endothelial barrier function.[14,15] It is generated by the phosphorylation of sphingosine catalyzed by sphingosine kinases (SphKs)[1,2] and metabolized by S1P) phosphatases and lipid phosphatases to yield sphingosine or by S1P) lyase (S1PL; Sgp11) that generates Δ2-hexadecenal and ethanolamine phosphate in mammalian cells.[16] In addition to the previously mentioned enzymes, serine palmitoyltransferase (SPT) initiates the biosynthesis of sphingolipids by catalyzing condensation of serine and palmitoyl-CoA to form 3-ketosphinganine.[17] S1P) acts extracellularly and intracellularly, and most effects of extracellular S1P are mediated via a family of five highly specific G-protein—coupled S1P1-5 receptors.[18,19] Significantly lower levels of S1P) in plasma and lung tissues were reported in a murine model of lipopolysaccharide (LPS)—induced lung injury, most likely because of elevated expression of S1PL,[20] and infusion of S1P) ameliorated LPS-induced acute lung injury in murine and canine models.[21,22] It is possible that S1P) plays a protective role in LPS-mediated lung injury. Hyperoxia is also known to cause lung injury, leading to a range of lung diseases. However, the underlying pathological characteristics are not similar to those observed in the LPS-treated mouse model.[20,23]

It was previously shown that plasma apolipoprotein M (ApoM)-containing HDL (ApoM+HDL) is a physiological carrier of the bioactive lipid sphingosine 1-phosphate (SIP). ApoM-S1P complexes activate G protein-coupled S1P receptors, suppressing inflammatory responses and maintains vascular barrier function. Mice that lack ApoM have alterations in lipoprotein metabolism and exhibit enhanced atherosclerosis in the LDL receptor null background. Various pathological conditions, including type I and II diabetes, cardiovascular diseases, infection, and conditions associated with endothelial injury, are associated with reduced level or activity of ApoM/S1P.

The activation of ApoM-S1P signaling pathway was shown to be able to be utilized in the treatment of a range of diseases, e.g., as described in PCT application No. PCT/US2018/000202, incorporated herein by reference. However, this strategy has not been shown to be effective in treating lung diseases.

The present disclosure is based, at least in part, on the novel finding that activation of the S1P signaling pathway by providing ApoM is effective in restoring lung architecture and promoting lung regeneration and growth in models of lung diseases. Free ApoM that is not associated with HDL has an extremely short half-life (e.g., as described in Faber et al., *Molecular Endocrinology* 20, 212-218, 2006, incorporated herein by reference). A fusion protein comprising an ApoM fused to a constant region (Fc) of an immunoglobulin G (IgG) the ApoM to a constant region (Fc) of an immunoglobulin was used in the compositions and methods described herein. Such ApoM-Fc fusion protein has been described in PCT application No. PCT/US2018/000202, incorporated herein by reference. Fusing ApoM to Fc stabilizes the ApoM in plasma. In some embodiments, the fusion protein further comprises a signal peptide, allowing the fusion protein to be secreted, e.g., into the culturing media, and purified.

Accordingly, some aspects of the present disclosure provide methods of treating a lung disease, the method comprising administering to a subject in need thereof a therapeutically effective amount of a fusion protein comprising an ApoM fused to a Fc of an IgG.

A "fusion protein" as used herein, refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A fusion protein may comprise different domains, for example, an ApoM domain and a Fc domain. In some embodiments, the ApoM is fused at the N-terminus of the Fc. In some embodiments, the ApoM is fused at the C-terminus of the Fc.

"Apolipoprotein M (ApoM)" is a 26-kDa protein that is mainly associated with high-density lipoprotein (HDL) in mammalian (e.g., human) plasma, with a small proportion present in triglyceride-rich lipoproteins (TGRLP) and low-density lipoproteins (LDL). It belongs to lipocalin protein superfamily. ApoM is only expressed in liver and in kidney and small amounts are found in fetal liver and kidney. Expression of native ApoM could be regulated by platelet activating factor (PAF), transforming growth factors (TGF), insulin-like growth factor (IGF) and leptin in vivo and/or in vitro. The ApoM may be from any mammal (e.g., a human or a murine such as a mouse or a rat). The amino acid sequences of wild-type human and mouse ApoM, and nucleotide sequences encoding such are provided in Table 1. It is to be understood that the sequences provided are for illustration purpose only and are not meant to be limiting.

In some embodiments, the ApoM comprises an amino acid sequence that is at least 70% identical to SEQ ID NO: 5 or SEQ ID NO: 6. For example, the ApoM may comprise an amino acid sequence that is at least 70%, at least 80%, at least 90%, at least 95%, or at least 99% identical to SEQ ID NO: 5 or SEQ ID NO: 6. In some embodiments, the ApoM comprises an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 5 or SEQ ID NO: 6. In some embodiments, the ApoM comprises the amino acid sequence of SEQ ID NO: 5 or SEQ ID NO 6. In some embodiments, the ApoM consists of the amino acid sequence of SEQ ID NO: 5 or SEQ ID NO 6.

A "constant region (Fc) of an immunoglobulin (Ig)" refers to a carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and in some embodiments, lacks the CH1 domain.

In some embodiments, the Fc is derived from a heavy chain constant region of an IgG (Igγ) (γ subclasses 1, 2, 3, or 4). In some embodiments, the Fc is derived from a heavy chain constant region of IgG1. Other classes of immunoglobulin, IgA (Igα), IgD (Igδ), IgE (Igε) and IgM (Igμ), may also be used. The choice of appropriate immunoglobulin heavy chain constant region is described in the art, e.g., in U.S. Pat. Nos. 5,541,087, and 5,726,044, incorporated herein by reference. The choice of particular immunoglobulin heavy chain constant region sequences from certain immunoglobulin classes and subclasses to achieve a particular result is considered to be within the level of skill in the art. In some embodiments, The portion of the DNA construct encoding the immunoglobulin Fc region preferably comprises at least a portion of a hinge domain, and preferably at least a portion of a CH3 domain of Fc γ or the homologous domains in any of IgA, IgD, IgE, or IgM. The immunoglobulin may be from any mammal (e.g., a human or a murine such as a mouse or a rat). In some embodiments, the Fc is from a human IgG (e.g., human IgG1). In some embodiments, the Fc is from a murrain IgG (e.g., murine IgG1). The amino acid sequences of Fc from human or murine IgG1, and nucleotide sequences encoding such are provided in Table 1. It is to be understood that the sequences provided are for illustration purpose only and are not meant to be limiting. Substitution or deletion of amino acids within the immunoglobulin heavy chain constant regions are also contemplated herein. A non-limiting example would be to introduce amino acid substitutions in the upper CH2 region to create an Fc variant with reduced affinity for Fc receptors (e.g., as described in Cole et al. (1997) *J. Immunol.* 159: 3613, incorporated herein by reference).

In some embodiments, the Fc comprises an amino acid sequence that is at least 70% identical to SEQ ID NO: 7 or SEQ ID NO: 8. For example, the Fc may comprise an amino acid sequence that is at least 70%, at least 80%, at least 90%, at least 95%, at least 99%, or at least 99.5% identical to SEQ ID NO: 7 or SEQ ID NO: 8. In some embodiments, the Fc comprises an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO: 7 or SEQ ID NO: 8. In some embodiments, the Fc comprises the amino acid sequence of SEQ ID NO: 7 or SEQ ID NO 8. In some embodiments, the Fc consists of the amino acid sequence of SEQ ID NO: 7 or SEQ ID NO 8.

In some embodiments, the fusion protein used in the methods described herein comprises a human ApoM fused to a human Fc (designated "hApoM-hFc" herein). In some embodiments, the fusion protein used in the methods described herein comprises a murine ApoM fused to a murine Fc (designated "mApoM-mFc" herein). In some embodiments, the fusion protein used in the methods described herein comprises a human ApoM fused to a murine Fc (designated "hApoM-mFc" herein). In some embodiments, the fusion protein described used in the methods herein comprises a murine ApoM fused to a human Fc (designated "mApoM-hFc" herein). While any of the fusion proteins described herein may be used in any subject (e.g., a human or a murine such as a mouse or a rat), using a fusion protein comprising domains that are from the same origin (e.g., species) as the subject may reduce unwanted immune response against the fusion protein in the subject. As such, in some embodiments, a fusion protein comprising a human ApoM fused to a human Fc is used in a human subject (e.g., for chronic administration for treating a lung disease). In some embodiments, a fusion protein comprising a murine (e.g., mouse) ApoM fused to a murine (e.g., mouse) Fc is used in a mouse (e.g., in a mouse model of a lung disease).

In some embodiments, the fusion protein further comprises a signal peptide. For example, in some embodiments, the signal peptide is fused at the N-terminus of ApoM. A "signal peptide" refers to a short peptide (e.g., 16-30 amino acids long) present at the N-terminus of a large number of newly synthesized proteins that are destined towards the secretory pathway. Signal peptides are typically needed for the translocation across the membrane on the secretory pathway and thus universally control the entry of most proteins both in eukaryotes and prokaryotes to the secretory pathway. Signal peptides generally include three regions: an N-terminal region of differing length, which usually comprises positively charged amino acids; a hydrophobic region; and a short carboxy-terminal peptide region. In eukaryotes, the signal peptide of a nascent precursor protein (preprotein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide may have a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

In some embodiments, the fusion protein of the present disclosure contains a signal peptide at the either the N- or C-terminus to facilitate secretion of the fusion protein. In some embodiments, the signal peptide is at the N-terminus of the fusion protein. For example, the fusion protein may have a signal peptide-ApoM-Fc structure. In some embodiments, the signal peptide fused to the fusion protein is an artificial signal peptide, e.g., an IL-2 signal peptide, an IgE signal peptide or an IgG signal peptide. In some embodiments, the signal peptide is an IL-2 signal peptide comprising the amino acid sequence of MYRMQLLSCIALSLA-LVTNS (SEQ ID NO: 15). In some embodiments, the signal peptide is an Ig heavy chain epsilon-1 signal peptide (IgE HC SP) comprising the amino acid sequence of MDWTWILFLVAAATRVHS (SEQ ID NO: 16). In some embodiments, a signal peptide is an IgGk chain V-III region HAH signal peptide (IgGk SP) comprising the amino acid sequence of (SEQ ID NO: 17)
METPAQLLFLLLLWLPDTTG.

In some embodiments, the fusion protein of the present disclosure comprises an amino acid sequence that is at least 70% identical to any one of SEQ ID NOs: 1-4 and 9. For example, the fusion protein may comprise an amino acid sequence that is at least 70%, at least 80%, at least 90%, at least 95%, at least 99%, or at least 99.5% identical to any one of SEQ ID NOs: 1-4 and 9. In some embodiments, the fusion protein comprises an amino acid sequence that is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to any one of SEQ ID NOs: 1-4 and 9. In some embodiments, the fusion protein comprises the amino acid sequence of any one of SEQ ID NOs: 1-4 and 9. In some embodiments, the fusion protein consists of the amino acid sequence of any one of SEQ ID NOs: 1-4 and 9.

The "percent identity" of two amino acid sequences is determined using the algorithm of Karlin and Altschul Proc.

Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NB LAST) can be used.

In some embodiments, the fusion protein used in the methods described herein comprises amino acid substitutions in one or both of the ApoM and Fc domains, compared to a wild type amino acid sequence of ApoM and/or Fc. The substitution mutations described herein will typically be replacement with a different naturally occurring amino acid residue, but in some cases non-naturally occurring amino acid residues may also be substituted. Non-natural amino acids, as the term is used herein, are non-proteinogenic (i.e., non-protein coding) amino acids that either occur naturally or are chemically synthesized. Examples include but are not limited to β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, and N-methyl amino acids. In some embodiments, the amino acid can be substituted or unsubstituted. The substituted amino acid or substituent can be a halogenated aromatic, or aliphatic amino acid, a halogenated aliphatic, or aromatic modification on the hydrophobic side chain, or an aliphatic or aromatic modification.

Amino acid substitution can be achieved during chemical synthesis of the peptide by adding the desired substitute amino acid at the appropriate sequence in the synthesis process. Alternatively, molecular biology methods can be used. Non-conservative substitutions are also encompassed to the extent that they substantially retain the activities of those peptides described herein.

In some embodiments, the amino acid substituted fusion protein will substantially retain the activity of the non-substituted fusion protein. "Substantially retain" means one or more activity of the variant is at least 50% compared to the activity of the original polypeptide in a similar assay, under similar conditions. In some embodiments, the activity is at least 60%, at least 70%, at least 80%, at least 90%, at least 95%, at least 99%, at least 100%, at least 2-fold, at least 5-fold, at least 10-fold, at least 100-fold or higher activity compared to the original fusion protein.

In some embodiments, a linker may be used to fuse the ApoM (e.g., wild type or variant) to the Fc, and/or to fuse the signal peptide to the rest of the fusion protein. A "linker" refers to a chemical group or a molecule linking two molecules or moieties, e.g., two domains of a fusion protein. Typically, the linker is positioned between, or flanked by, two groups, molecules, domains, or other moieties and connected to each one via a covalent bond, thus connecting the two. The linker may be as simple as a covalent bond, or it may be a polymeric linker many atoms in length. In some embodiments, the linker is a polypeptide or based on amino acids. In some embodiments, the linker is not peptide-like. In some embodiments, the linker is a covalent bond (e.g., a carbon-carbon bond, disulfide bond, carbon-heteroatom bond, etc.). In some embodiments, the linker is a carbon-nitrogen bond of an amide linkage. In some embodiments, the linker is a cyclic or acyclic, substituted or unsubstituted, branched or unbranched aliphatic or heteroaliphatic linker. In some embodiments, the linker is polymeric (e.g., polyethylene, polyethylene glycol, polyamide, polyester, etc.). In some embodiments, the linker comprises a monomer, dimer, or polymer of aminoalkanoic acid. In some embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In some embodiments, the linker comprises a monomer, dimer, or polymer of aminohexanoic acid (Ahx). In some embodiments, the linker is based on a carbocyclic moiety (e.g., cyclopentane, cyclohexane). In other embodiments, the linker comprises a polyethylene glycol moiety (PEG). In other embodiments, the linker comprises amino acids. In some embodiments, the linker comprises a peptide. In some embodiments, the linker comprises an aryl or heteroaryl moiety. In some embodiments, the linker is based on a phenyl ring. The linker may include functionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates.

In some embodiments, the linker is an amino acid or a plurality of amino acids (e.g., a peptide or protein). In some embodiments, the linker is a bond (e.g., a covalent bond), an organic molecule, group, polymer, or chemical moiety. In some embodiments, the linker is 1-100 amino acids in length, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-110, 110-120, 120-130, 130-140, 140-150, or 150-200 amino acids in length. Longer or shorter linkers are also contemplated.

In some embodiments, a linker comprises the amino acid sequence SGSETPGTSESATPES (SEQ ID NO: 18), which may also be referred to as the XTEN linker. In some embodiments, a linker comprises the amino acid sequence. In some embodiments, a linker comprises $(SGGS)_n$ (SEQ ID NO: 19), $(GGGS)_n$ (SEQ ID NO: 20), $(GGGGS)_n$ (SEQ ID NO: 21), $(G)_n$ (SEQ ID NO: 22), $(EAAAK)_n$ (SEQ ID NO: 23), $(GGS)_n$ (SEQ ID NO: 24), SGSETPGTSESATPES (SEQ ID NO: 18), or $(XP)_n$ motif, or a combination of any of these, wherein n is independently an integer between 1 and 30, and wherein X is any amino acid. In some embodiments, n is 1, 2, 3, 4, 5, 6, 7, 8, 9, 10, 11, 12, 13, 14, or 15. In some embodiments, a linker comprises SGSETPGTSESATPES (SEQ ID NO: 18), and SGGS (SEQ ID NO: 25). In some embodiments, a linker comprises SGGSSGSETPGTSESATPESSGGS (SEQ ID NO: 26). In some embodiments, a linker comprises SGGSSGGSSGSETPGTSESATPESSGGSGGS (SEQ ID NO: 27). In some embodiments, a linker comprises (SEQ ID NO: 28)
GGSGGSPGSPAGSPTSTEEGTSESATPESGPGTSTEPSEGSAPGSPAGS

PTSTEEGTSTEPSEGSAPGTSTEPSEGSAPGTSESATPESGPGSEPATS

GGSGGS.

In some embodiments, the fusion protein used in the methods described herein comprises a modification. When the fusion protein is referred to herein, it encompasses all its variants and derivatives. Polypeptides comprising modifications have additional features other than amino acid contents. As used herein, a "modification" or "derivative" of a protein or polypeptide (e.g., the fusion protein used in the methods described herein) produces a modified or derivatized polypeptide, which is a form of a given peptide that is chemically modified relative to the reference peptide, the modification including, but not limited to, oligomerization or polymerization, modifications of amino acid residues or peptide backbone, cross-linking, cyclization, conjugation, PEGylation, glycosylation, acetylation, phosphorylation, acylation, carboxylation, lipidation, thioglycolic acid amidation, alkylation, methylation, polyglycylation, glycosylation, polysialylation, adenylylation, PEGylation, fusion to additional heterologous amino acid sequences, or other modifications that substantially alter the stability, solubility, or other properties of the peptide while substantially retaining the activity of the polypeptides described herein. It is to be understood that the fusion protein comprising such modifications, are cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combination thereof. In some embodiments, the modified fusion protein of the present disclosure may contain non-amino acid elements, such as polyethylene glycols, lipids, poly- or mono-saccharide, and phosphates. The fusion protein of the present disclosure, may comprise the modifications disclosed herein at the C-terminus (e.g., C-terminal amidation), N-terminus (e.g., N-terminal acetylation). Terminal modifications are useful, and are well known, to reduce susceptibility to proteinase digestion, and therefore serve to prolong half-life of the polypeptides in solutions, particularly biological fluids where proteases may be present. In some embodiments, the fusion protein used in the methods described herein are further modified within the sequence, such as, modification by terminal-$NH_2$ acylation, e.g., acetylation, or thioglycolic acid amidation, by terminal-carboxylamidation, e.g., with ammonia, methylamine, and the like terminal modifications.

Terminal modifications are useful, to reduce susceptibility by proteinase digestion, and therefore can serve to prolong half-life of the polypeptides in solution, particularly in biological fluids where proteases may be present. Amino terminus modifications include methylation (e.g., —$NHCH_3$ or —$N(CH_3)_2$), acetylation (e.g., with acetic acid or a halogenated derivative thereof such as a-chloroacetic acid, a-bromoacetic acid, or a-iodoacetic acid), adding a benzyloxycarbonyl (Cbz) group, or blocking the amino terminus with any blocking group containing a carboxylate functionality defined by RCOO— or sulfonyl functionality defined by R—$SO_2$-, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the polypeptide. In certain embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the peptides described herein, or incorporate a desamino or descarboxy residue at the termini of the peptide, so that there is no terminal amino or carboxyl group, to decrease susceptibility to proteases or to restrict the conformation of the peptide. Methods of circular peptide synthesis are known in the art, for example, in U.S. Patent Application No. 20090035814; Muralidharan and Muir, 2006, Nat Methods, 3:429-38; and Lockless and Muir, 2009, Proc Natl Acad Sci USA. June 18, Epub. C-terminal functional groups of the peptides described herein include amide, amide lower alkyl, amide di(lower alkyl), lower alkoxy, hydroxy, and carboxy, and the lower ester derivatives thereof, and the pharmaceutically acceptable salts thereof.

In some embodiments, the fusion protein used in the methods described herein is phosphorylated. One can also readily modify peptides by phosphorylation, and other methods (e.g., as described in Hruby, et al. (1990) Biochem J. 268:249-262). In some embodiments, one can also replace the naturally occurring side chains of the genetically encoded amino acids (or the stereoisomeric D amino acids) with other side chains, for instance with groups such as alkyl, lower (C1-6) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocycles. For example, proline analogues in which the ring size of the proline residue is changed from 5 members to 4, 6, or 7 members can be employed.

Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl.

In some embodiments, the fusion protein used in the methods described herein may be attached to one or more polymer moieties. In some embodiments, these polymers are covalently attached to the fusion proteins of the disclosure. In some embodiments, for therapeutic use of the end product preparation, the polymer is pharmaceutically acceptable. One skilled in the art will be able to select the desired polymer based on such considerations as whether the polymer-peptide conjugate will be used therapeutically, and if so, the desired dosage, circulation time, resistance to proteolysis, and other considerations.

Suitable polymers include, for example, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Such a polymer may or may not have its own biological activity. The polymers can be covalently or non-covalently conjugated to the fusion protein. Methods of conjugation for increasing serum half-life and for radiotherapy are known in the art, for example, in U.S. Pat. Nos. 5,180,816, 6,423,685, 6,884,780, and 7,022,673, which are hereby incorporated by reference in their entirety.

In some embodiments, the fusion protein used in the methods described herein may be attached to one or more water soluble polymer moieties. The water soluble polymer may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl-pyrrolidone) polyethylene glycol, propropylene glycol homopolymers, polypropylene oxide/ethylene oxide copolymers, and polyoxyethylated polyols. A preferred water soluble polymer is PEG.

The polymer may be of any molecular weight, and may be branched or unbranched. The average molecular weight of the reactant PEG is preferably between about 3,000 and about 50,000 daltons (the term "about" indicating that in preparations of PEG, some molecules will weigh more, and some less, than the stated molecular weight). More preferably, the PEG has a molecular weight of from about 10 kDa to about 40 kDa, and even more preferably, the PEG has a molecular weight from 15 to 30 kDa. Other sizes may be used, depending on the desired therapeutic profile (e.g., duration of sustained release desired; effects, if any, on biological activity; ease in handling; degree or lack of antigenicity; and other effects of PEG on a therapeutic peptide known to one skilled in the art).

The number of polymer molecules attached may vary; for example, one, two, three, or more water-soluble polymers may be attached to a peptide of the disclosure. The multiple attached polymers may be the same or different chemical moieties (e.g., PEGs of different molecular weight).

In certain embodiments, PEG may be attached to at least one terminus (N-terminus or C-terminus) of the fusion protein used in the methods described herein. In some embodiments, PEG may be attached to a linker moiety of the fusion protein. In some embodiments, the linker contains more than one reactive amine capable of being derivatized with a suitably activated PEG species.

PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins. PEGylation, by increasing the molecular weight of a molecule, can impart several significant pharmacological advantages over the unmodified form, such as: improved drug solubility, reduced dosage frequency, without diminished efficacy with potentially reduced toxicity, extended circulating life, increased drug stability, and enhanced protection from proteolytic degradation. In addition, PEGylated drugs are have wider opportunities for new delivery formats and dosing regimens. Methods of PEGylating molecules, proteins and peptides are well known in the art, e.g., as described in U.S. Pat. Nos. 5,766,897; 7,610,156; 7,256,258 and the International Application No. WO/1998/032466.

In some embodiments, the fusion protein is conjugated to another moiety. For example, the fusion proteins can be conjugated to other polymers in addition to polyethylene glycol (PEG). The polymer may or may not have its own biological activity. Further examples of polymer conjugation include but are not limited to polymers such as polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and $\alpha,\beta$-Poly [(2-hydroxyethyl)-DL-aspartamide, and the like, or mixtures thereof. Conjugation to a polymer can improve serum half-life, among other effects. A variety of chelating agents can be used to conjugate the peptides described herein. These chelating agents include but are not limited to ethylenediaminetetraacetic acid (EDTA), diethylenetriaminopentaacetic acid (DTPA), ethyleneglycol-0,0'-bis(2-aminoethyl)-N,N,N',N'-tetraacetic acid (EGTA), N,N'-bis (hydroxybenzyl)ethylenediamine-N,N'-diacetic acid (HBED), triethylenetetraminehexaacetic acid (TTHA), 1,4,7,10-tetra-azacyclododecane-N,N',N'',N'''-tetraacetic acid (DOTA), 1,4,7,10-tetraazacyclotridecane-1,4,7,10-tetraacetic acid (TITRA), 1,4,8,11-tetraazacyclotetradecane-N,N',N'',N'''-tetraacetic acid (TETA), and 1,4,8,11-tetraazacyclotetradecane (TETRA). Methods of conjugation are well known in the art, for example, P. E. Thorpe, et. al, 1978, Nature 271, 752-755; Harokopakis E., et. al., 1995, Journal of Immunological Methods, 185:31-42; S. F. Atkinson, et. al., 2001, J. Biol. Chem., 276:27930-27935; and U.S. Pat. Nos. 5,601,825, 5,180,816, 6,423,685, 6,706,252, 6,884,780, and 7,022,673, which are hereby incorporated by reference in their entirety.

Other methods for stabilizing peptides known in the art may be used with the methods and compositions described herein. For example, using D-amino acids, using reduced amide bonds for the peptide backbone, and using non-peptide bonds to link the side chains, including, but not limited to, pyrrolinone and sugar mimetics can each provide stabilization. The design and synthesis of sugar scaffold peptide mimetics are described by Hirschmann et al. (J. Med. Chem., 1996, 36, 2441-2448, which is incorporated herein by reference in its entirety). Further, pyrrolinone-based peptide mimetics present the peptide pharmacophore on a stable background that has improved bioavailability characteristics (see, for example, Smith et al., J. Am. Chem. Soc. 2000, 122, 11037-11038), which is incorporated herein by reference in its entirety.

All combinations of the different modifications and derivatizations are envisioned for the fusion protein used in the methods described herein. Modifications, derivatives and methods of reprivatizing polypeptides are described in Published International Application WO 2010/014616, the contents of which are incorporated herein by reference.

Methods of producing the fusion protein are also provided. The fusion protein will generally be produced by expression form recombinant nucleic acids in appropriate cells (e.g., bacterial cell or eukaryotic cells) and isolated. To produce the fusion protein, nucleic acids encoding the fusion protein may be introduced to a cell (e.g., a bacterial cell or a eukaryotic cell such as a yeast cell or an insect cell. The cells may be cultured under conditions that allow the fusion protein to express from the nucleic acids encoding the fusion protein. Fusion proteins comprising a signal peptide can be secreted, e.g., into the culturing media and can subsequently be recovered. The fusion protein may be isolated using any methods of purifying a protein known in the art.

The nucleic acids encoding the fusion protein used in the methods described herein may be obtained, and the nucleotide sequence of the nucleic acids determined, by any method known in the art. Non-limiting, exemplary nucleotide sequence encoding the fusion protein or variants described herein are provided in Table 1. One skilled in the art is able to identify the nucleotide sequence encoding the fusion protein from the amino acid sequence of the fusion protein. The nucleic acids encoding the fusion protein of the present disclosure, may be DNA or RNA, double-stranded or single stranded. In some embodiments, the nucleotide sequence encoding the fusion protein may be codon optimized to adapt to different expression systems (e.g., for mammalian expression).

In some embodiments, the nucleic acid is comprised within a vector, such as an expression vector. In some embodiments, the vector comprises a promoter operably linked to the nucleic acid.

A variety of promoters can be used for expression of the fusion protein used in the methods described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, E. coli lac UV5 promoter, and the herpes simplex tk virus promoter.

Regulatable promoters can also be used. Such regulatable promoters include those using the lac repressor from E. coli as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from Escherichia coli can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used (Yao et al., Human Gene Therapy; Gossen et al., Natl. Acad. Sci. USA, 89:5547-5551 (1992); Shockett et al., Proc. Natl. Acad. Sci. USA, 92:6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the fusion protein used in the methods described herein. In some embodiments, the expression of the fusion protein used in the methods described herein is regulated by a constitutive, an inducible or a tissue-specific promoter.

The host cells used to express the fusion protein used in the methods described herein may be either bacterial cells such as Escherichia coli, or, preferably, eukaryotic cells. In particular, mammalian cells, such as Chinese hamster ovary cells (CHO), in conjunction with a vector such as the major intermediate early gene promoter element from human cytomegalovirus is an effective expression system for immunoglobulins (Foecking et al. (1986) "Powerful And Versatile Enhancer-Promoter Unit For Mammalian Expression Vectors," Gene 45:101-106; Cockett et al. (1990) "High Level Expression Of Tissue Inhibitor Of Metalloproteinases In Chinese Hamster Ovary Cells Using Glutamine Synthetase Gene Amplification," Biotechnology 8:662-667).

A variety of host-expression vector systems may be utilized to express the fusion protein used in the methods described herein. Such host-expression systems represent vehicles by which the coding sequences of the isolated fusion protein used in the methods described herein may be produced and subsequently purified, but also represent cells which may, when transformed or transfected with the appropriate nucleotide coding sequences, express the fusion protein used in the methods described herein in situ. These include, but are not limited to, microorganisms such as bacteria (e.g., E. coli and B. subtilis) transformed with recombinant bacteriophage DNA, plasmid DNA or cosmid DNA expression vectors containing coding sequences for the fusion protein used in the methods described herein; yeast (e.g., Saccharomyces pichia) transformed with recombinant yeast expression vectors containing sequences encoding the fusion protein used in the methods described herein; insect cell systems infected with recombinant virus expression vectors (e.g., baclovirus) containing the sequences encoding the fusion protein used in the methods described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the fusion protein used in the methods described herein; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the fusion proteins being expressed. For example, when a large quantity of such a protein is to be produced, for the generation of pharmaceutical compositions of fusion protein described herein, vectors which direct the expression of high levels of fusion protein products that are readily purified may be desirable. Such vectors include, but are not limited, to the E. coli expression vector pUR278 (Rüther et al. (1983)

"Easy Identification Of cDNA Clones," EMBO J. 2:1791-1794), in which the coding sequence may be ligated individually into the vector in frame with the lac Z coding region so that a fusion protein is produced; pIN vectors (Inouye et al. (1985) "Up-Promoter Mutations In The 1pp Gene Of *Escherichia Coli*," Nucleic Acids Res. 13:3101-3110; Van Heeke et al. (1989) "Expression Of Human Asparagine Synthetase In *Escherichia Coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Purification and modification of recombinant proteins is well known in the art such that the design of the polyprotein precursor could include a number of embodiments readily appreciated by a skilled worker. Any known proteases or peptidases known in the art can be used for the described modification of the precursor molecule, e.g., thrombin or factor Xa (Nagai et al. (1985) "Oxygen Binding Properties Of Human Mutant Hemoglobins Synthesized In *Escherichia Coli*," Proc. Nat. Acad. Sci. USA 82:7252-7255, and reviewed in Jenny et al. (2003) "A Critical Review Of The Methods For Cleavage Of Fusion Proteins With Thrombin And Factor Xa," Protein Expr. Purif. 31:1-11, each of which is incorporated by reference herein in its entirety)), enterokinase (Collins-Racie et al. (1995) "Production Of Recombinant Bovine Enterokinase Catalytic Subunit In *Escherichia Coli* Using The Novel Secretory Fusion Partner DsbA," Biotechnology 13:982-987 hereby incorporated by reference herein in its entirety)), furin, and AcTEV (Parks et al. (1994) "Release Of Proteins And Peptides From Fusion Proteins Using A Recombinant Plant Virus Proteinase," Anal. Biochem. 216:413-417 hereby incorporated by reference herein in its entirety)) and the Foot and Mouth Disease Virus Protease C3.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express the fusion protein used in the methods described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the fusion protein used in the methods described herein. Such engineered cell lines may be particularly useful in screening and evaluation of fusion proteins that interact directly or indirectly with the fusion protein used in the methods described herein.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11: 223-232), hypoxanthine-guanine phosphoribosyltransferase (Szybalska et al. (1992) "Use Of The HPRT Gene And The HAT Selection Technique In DNA-Mediated Transformation Of Mammalian Cells First Steps Toward Developing Hybridoma Techniques And Gene Therapy," Bioessays 14: 495-500), and adenine phosphoribosyltransferase (Lowy et al. (1980) "Isolation Of Transforming DNA: Cloning The Hamster aprt Gene," Cell 22: 817-823) genes can be employed in tk–, hgprt– or aprt– cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. USA 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. USA 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. USA 78: 2072-2076); neo, which confers resistance to the aminoglycoside G-418 (Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human Gene Therapy," Ann. Rev. Biochem. 62:191-217) and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al. (1981) "A New Dominant Hybrid Selective Marker For Higher Eukaryotic Cells," J. Mol. Biol. 150:1-14.

The expression levels of the fusion described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a fusion protein used in the methods described herein is amplifiable, increase in the level of inhibitor present in culture of host cell will increase the number of copies of the marker gene.

Once a fusion protein used in the methods described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the polypeptide comprises an Fc domain (or portion thereof)), and sizing column chromatography), centrifugation, differential solubility, or by any other standard technique for the purification of polypeptides or antibodies.

In some embodiments, to facilitate purification, e.g., by affinity chromatography, the fusion protein used in the methods described herein further contains a fusion domain. Well known examples of such fusion domains include, without limitation, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners.

In some embodiments, the fusion protein used in the methods described herein is formulated in a pharmaceutical composition for administration to a subject for treating a lung disease. A "pharmaceutical composition," as used herein, refers to the formulation of the fusion protein used in the methods described herein in combination with a pharmaceutically acceptable carrier. The pharmaceutical composition can further comprise additional agents (e.g. for specific delivery, increasing half-life, or other therapeutic agents).

The term "pharmaceutically-acceptable carrier", as used herein, means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the fusion protein from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, an fusion protein is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the fusion protein of the disclosure does not absorb are used.

In other embodiments, the fusion protein is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol.

25:351; Howard et al., 1989, J. Neurosurg. 71:105.) Other controlled release systems are discussed, for example, in Langer, supra.

The fusion protein can be administered as pharmaceutical compositions comprising a therapeutically effective amount of a binding agent and one or more pharmaceutically compatible ingredients.

In some embodiments, the pharmaceutical composition is formulated in accordance with routine procedures as a pharmaceutical composition adapted for intravenous or subcutaneous administration to a subject, e.g., a human being. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. The fusion proteins of the present disclosure can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N, N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757.

The pharmaceutical compositions of the present disclosure may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

In some embodiments, the pharmaceutical composition can be provided as a pharmaceutical kit comprising (a) a container containing a fusion protein of the disclosure in lyophilized form and (b) a second container containing a pharmaceutically acceptable diluent (e.g., sterile water) for injection. The pharmaceutically acceptable diluent can be used for reconstitution or dilution of the lyophilized fusion protein of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is an fusion protein of the disclosure. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

The terms "treatment" or "to treat" refer to both therapeutic and prophylactic treatments. If the subject is in need of treatment of cancer (as a disease associated with excess S1P), then "treating the condition" refers to ameliorating, reducing or eliminating one or more symptoms associated with the cancer or the severity of cancer or preventing any further progression of cancer. If the subject in need of treatment is one who is at risk of having cancer, then treating the subject refers to reducing the risk of the subject having cancer or preventing the subject from developing cancer.

A subject shall mean a human or vertebrate animal or mammal including but not limited to a rodent, e.g., a rodent such as a rat or a mouse, dog, cat, horse, cow, pig, sheep, goat, turkey, chicken, and primate, e.g., monkey. In some embodiments, the subject is human. In some embodiments, the subject is a companion animal. "A companion animal," as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. The methods of the present disclosure are useful for treating a subject in need thereof. A subject in need thereof can be a subject who has or is has a risk of developing a lung disease.

In some embodiments, the subject in need thereof is a human subject having or at risk of developing a lung disease. In some embodiments, the human subject is a human fetus (i.e., before the subject is born). In some embodiments, the subject is a human neonate. As used herein, a human neonate refers to a human from the time of birth to about 4 weeks of age. In some embodiments, the subject is a human infant. As used herein, a human infant refers to a human from about the age of 4 weeks of age to about 3 years of age. In some embodiments, the subject is a human subject that is between 3-18 years of age (e.g., 3, 4, 5, 6, 7, 8, 9, 10, 11, 12, 13, 14, 15, 16, 17, or 18 years of age). In some embodiments, the subject is 3-18, 3-17, 3-16, 3-15, 3-14, 3-13, 3-12, 3-11, 3-10, 3-9, 3-8, 3-7, 3-6, 3-5, 3-4, 4-18, 4-17, 4-16, 4-15, 4-14, 4- 13, 4-12, 4-11, 4-10, 4-9, 4-8, 4-7, 4-6, 4-5, 5-18, 5-17, 5-16, 5-15, 5-14, 5-13, 5-12, 5-11, 5-10, 5-9, 5-8, 5-7, 5-6, 6-18, 6-17, 6-16, 6-15, 6-14, 6-13, 6-12, 6-11, 6-10, 6-9, 6-8, 6-7, 7-18, 7-17, 7-16, 7-15, 7-14, 7-13, 7-12, 7-11, 7-10, 7-9, 7-8, 8-18, 8-17, 8-16, 8-15, 8-14, 8-13, 8-12, 8- 11, 8-10, 8-9, 9-18, 9-17, 9-16, 9-15, 9-14, 9-13, 9-12, 9-11, 9-10, 10-18, 10-17, 10-16, 10-15, 10-14, 10-13, 10-12, 10-11, 11-18, 11-17, 11-16, 11-15, 11-14, 11-13, 11-12, 12-18, 12-17, 12-16, 12-15, 12-14, 12-13, 13-18, 13-17, 13-16, 13-15, 13-14, 14-18, 14-17, 14-16, 14-15, 15-18, 15-17, 15-16, 16-18, 16-17, or 17-18 years of age. In some embodiments, the subject is a human adult (e.g., 18 years of age or older). In some embodiments, the subject is a human elderly (e.g., 65 years of age or older).

In some embodiments, the subject is born prematurely (also referred to herein as having a "low gestational age"). Low gestational age refers to birth (or delivery) that occurs before a normal gestational term for a given species. In humans, a full gestational term is about 40 weeks and may range from 37 weeks to more than 40 weeks. Low gestational age, in humans, akin to a premature birth is defined as birth that occurs before 37 weeks of gestation. The disclosure therefore contemplates prevention and/or treatment of subjects born before 37 weeks of gestation, including those born at even shorter gestational terms (e.g., before 36, before 35, before 34, before 33, before 32, before 31, before 30, before 29, before 28, before 27, before 26, before 25, before 24, before 23, or before 22 weeks of gestation).

The present disclosure contemplates treating a human subject in various stages, e.g., from when the subject is in utero to adulthood. With respect to neonates and particularly low gestation age neonates, the disclosure contemplates administration of the fusion protein within 1 year, 11 months, 10 months, 9 months, 8 months, 7 months, 6 months, 5 months, 4 months, 3 months, 2 months, 1 month, 4 weeks, 3 weeks, 2 weeks, 1 week, 6 days, 5 days, 4 days, 3 days, 2 days, 1 day, 12 hours, 6 hours, 3 hours, or 1 hour after birth. In some embodiments, the isolated MSC exosomes are administered within 1 hour of birth (e.g., within 1 hour, within 55 minutes, within 50 minutes, within 45 minutes, within 40 minutes, within 35 minutes, within 30 minutes, within 25 minutes, within 20 minutes, within 15 minutes, within 10 minutes, within 5 minutes, or within 1 minute). In some embodiments, the fusion protein is administered to the subject immediately after birth. The fusion protein may also be administered before birth, e.g., administering to the uterus of the mother.

In some embodiments, the fusion protein is administered to a subject (e.g., a neonate) once. In some embodiments, repeated administration of the fusion protein, including two, three, four, five or more administrations of the MSC exosomes, is contemplated. In some instances, the fusion protein may be administered continuously. Repeated or continuous administration may occur over a period of several hours (e.g., 1-2, 1-3, 1-6, 1-12, 1-18, or 1-24 hours), several days (e.g., 1-2, 1-3, 1-4, 1-5, 1-6 days, or 1-7 days) or several weeks (e.g., 1-2 weeks, 1-3 weeks, or 1-4 weeks) depending on the severity of the condition being treated. If administration is repeated but not continuous, the time in between administrations may be hours (e.g., 4 hours, 6 hours, or 12 hours), days (e.g., 1 day, 2 days, 3 days, 4 days, 5 days, or 6 days), or weeks (e.g., 1 week, 2 weeks, 3 weeks, or 4 weeks). The time between administrations may be the same or they may differ.

Pharmaceutically compositions that may be used in accordance with the present disclosure may be administered to a subject in need thereof in a therapeutically effective amount. The term "therapeutically effective amount" refers to the amount necessary or sufficient to realize a desired biologic effect. For example, a therapeutically effective amount of a cancer-target liposome associated with the present disclosure may be that amount sufficient to ameliorate one or more symptoms of the disease or disorder. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular pharmaceutically compositions being administered the size of the subject, or the severity of the disease or condition. One of ordinary skill in the art can empirically determine the effective amount of a particular therapeutic compound associated with the present disclosure without necessitating undue experimentation.

Subject doses of the fusion protein used in the methods described herein for delivery typically range from about 0.1 µg to 10 mg per administration, which depending on the application could be given daily, weekly, or monthly and any other amount of time there between. In some embodiments a single dose is administered during the critical consolidation or reconsolidation period. The doses for these purposes may range from about 10 µg to 5 mg per administration, and most typically from about 100 µg to 1 mg, with 2-4 administrations being spaced, for example, days or weeks apart, or more. In some embodiments, however, parenteral doses for these purposes may be used in a range of 5 to 10,000 times higher than the typical doses described above.

In some embodiments, a fusion protein of the present disclosure is administered at a dosage of between about 1 and 10 mg/kg of body weight of the mammal. In other embodiments, a fusion protein of the present disclosure is administered at a dosage of between about 0.001 and 1 mg/kg of body weight of the mammal. In yet other embodiments, a fusion protein of the present disclosure is administered at a dosage of between about 10-100 ng/kg, 100-500 ng/kg, 500 ng/kg-1 mg/kg, or 1-5 mg/kg of body weight of the mammal, or any individual dosage therein.

The formulations of the present disclosure are administered in pharmaceutically acceptable solutions, which may routinely contain pharmaceutically acceptable concentrations of salt, buffering agents, preservatives, compatible carriers, and optionally other therapeutic ingredients.

Administering the pharmaceutical composition of the present disclosure may be accomplished by any means known to the skilled artisan. In some embodiments, the fusion protein is administered subcutaneously, intracutaneously, intravenously, intramuscularly, intraarticularly, intraarterially, intrasynovially, intrasternally, intrathecally, intralesionally, intracranially, intratracheally, intramuscularly, or by inhalation. In some embodiments, the fusion protein is administered by inhalation using a mechanical device. In some embodiments, the fusion protein is administered topically. For example, the fusion protein may be put in the endotracheal tube, be administered during tracheostomy while the patient is ventilated so it goes to the distal airways. For delivery using a mechanical device, the fusion protein may be in a lipid formulation (e.g., a lipid that is a surfactant).

For oral administration, the fusion protein of the present disclosure can be formulated readily by combining the active compound(s) with pharmaceutically acceptable carriers well known in the art. Such carriers enable the compounds of the present disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers, i.e., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189). Other polymers that could be used are poly-1,3-dioxolane and poly-1,3,6-tioxocane. Preferred for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the therapeutic agent or by release of the biologically active material beyond the stomach environment, such as in the intestine.

To ensure full gastric resistance a coating impermeable to at least pH 5.0 is preferred. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

The fusion protein can be included in the formulation as fine multi particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the therapeutic agent may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the therapeutic agent either alone or as a mixture in different ratios.

Pharmaceutical preparations which can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The pharmaceutical compositions of the present disclosure, when desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the fusion protein may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The pharmaceutical compositions of the present disclosure and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The present disclosure contemplates the use of the ApoM-Fc fusion protein in the treatment of a range of lung diseases in a subject in need thereof. In some embodiments, the subject has be exposed to hyproxia. For example, the subject may have been put on a ventilator (e.g., as a neonate, infant, or adult). In some embodiments, the hyperoxia causes inflammation or injury to the lungs. In some embodiments, the subject has loss of vasculature of the lungs (e.g., without limitation) a moyamoya patient that has loss of vasculature of the lungs). In some embodiments, the subject has undergone a surgical intervention, e.g., without limitation, a partial or complete pneumonectomy (e.g., due to a disease such as lung cancer, emphysema, or pulmonary fibrosis). In some embodiments, the subject has chest wall constriction that restricts lung growth. The present disclosure contemplates the alleviation of chest wall constriction without the need of a rib expander to allow lung growth. In some embodiments, the subject has lung injury from inhalation of fire, smoke, and/or a toxic substance. The examples provided herein are for illustration purpose only and are not meant to be limiting. Any lung disease that have the underlying pathology of inflammation, injury, loss of vasculature, and/or restricted growth may be treated using the compositions and methods described herein.

In some embodiments, the subject in need thereof has or is at risk of developing a lung disease selected from: without limitation, bronchopulmonary dysplasia (BPD), chronic obstructive pulmonary disease (COPD), congenital diaphragmatic hernia (CDH), pulmonary hypertension, pulmonary hypoplasia, pulmonary fibrosis, emphysema, and asthma.

Bronchopulmonary dysplasia (BPD) is a condition that afflicts neonates who have been given oxygen or have been on ventilators, or neonates born prematurely particularly those born very prematurely (e.g., those born before 32 weeks of gestation). It is also referred to as neonatal chronic lung disease. Causes of BPD include mechanical injury for example as a result of ventilation, oxygen toxicity for example as a result of oxygen therapy, and infection. The disease may progress from non-inflammatory to inflammatory with time. Symptoms include bluish skin, chronic cough, rapid breathing, and shortness of breath. Subjects having BPD are more susceptible to infections such as respiratory syncytial virus infection. Subjects having BPD may develop pulmonary hypertension.

Chronic obstructive pulmonary disease (COPD) is a chronic inflammatory lung disease that causes obstructed airflow from the lungs. Symptoms include breathing difficulty, cough, mucus (sputum) production and wheezing. It's caused by long-term exposure to irritating gases or particulate matter, most often from cigarette smoke. People with COPD are at increased risk of developing heart disease, lung cancer and a variety of other conditions.

Congenital diaphragmatic hernia (CDH) is a birth defect of the diaphragm. The most common type of CDH is a Bochdalek hernia; other types include Morgagni hernia, diaphragm eventration and central tendon defects of the diaphragm. Malformation of the diaphragm allows the abdominal organs to push into the chest cavity, hindering proper lung formation. CDH is a life-threatening pathology in infants and a major cause of death due to two complications: pulmonary hypoplasia and pulmonary hypertension. Experts disagree on the relative importance of these two conditions, with some focusing on hypoplasia, others on hypertension. Newborns with CDH often have severe respiratory distress which can be life-threatening unless treated appropriately.

Pulmonary hypertension (PH) is a lung disease characterized by blood pressure in the pulmonary artery that is far above normal levels. Symptoms include shortness of breath, chest pain particularly during physical activity, weakness, fatigue, fainting, light headedness particularly during exercise, dizziness, abnormal heart sounds and murmurs, engorgement of the jugular vein, retention of fluid in the abdomen, legs and ankles, and bluish coloring in the nail bed.

Pulmonary hypoplasia is incomplete development of the lungs, resulting in an abnormally low number or size of bronchopulmonary segments or alveoli. A congenital malformation, it most often occurs secondary to other fetal abnormalities that interfere with normal development of the lungs.

Pulmonary fibrosis (PF) is a chronic and progressive lung disease where the air sac in the lungs (alveoli) becomes scarred and stiff making it difficult to breathe and get enough oxygen into the bloodstream.

Emphysema is a condition in which the alveoli at the end of the smallest air passages (bronchioles) of the lungs are destroyed as a result of damaging exposure to cigarette smoke and other irritating gases and particulate matter.

In some embodiments, once administered to a subject, the fusion protein activates a S1P) receptor in the subject. In some embodiments, the S1P) receptor is S1P1. "Activates a S1P) receptor" means the S1P) signaling is increased by at least 20% (e.g., at least 30%, at least 40%, at least 50%, at least 60%, at least 70%, at least 80%, at least 90%, at least 100%, at least 2-fold, at least 5-fold, at least 10-fold, at least 100-fold, or more).

In some embodiments, once administered to a subject, the fusion protein restores lung architecture. In some embodiments, lung architecture is considered to be "restored" when the architecture of the lung, e.g., as indicated by the overall integrity of the alveoli, is increased by at least 20% in subjects that have been administered the fusion protein, compared to in subjects that have not been administered the fusion protein. For example, lung architecture may be considered "restored" when the architecture of the lung, e.g., as indicated by the overall integrity of the alveoli, is increased by at least 10%, at least 20%, at least 30%, at least 40%, at least 50%, at least 70%, at least 80%, at least 90%, at least 100%, at least 2-fold, at least 5-fold, at least 10-fold, at least 50-fold, at least 100-fold or more, in subjects that have been administered the fusion protein, compared to in subjects that have not been administered the fusion protein. In some embodiments, lung architecture is considered "restored" when the architecture of the lung, e.g., as indicated by the overall integrity of the alveoli, is increased by 10%, 20%, 30%, 40%, 50%, 70%, 80%, 90%, 100%, 2-fold, 5-fold, 10-fold, 50-fold, 100-fold or more, in subjects that have been administered the fusion protein, compared to in subjects that have not been administered the fusion protein.

In some embodiments, once administered to a subject, the fusion protein increases lung regeneration and growth. In some embodiments, once administered to a subject, the fusion protein restore lung development. In some embodiments, lung regeneration and growth is considered to be increased, and/or lung development is considered to be "restored" when the size and/or function of the lung is increased by at least 20% in subjects that have been administered the fusion protein, compared to in subjects that have not been administered the fusion protein. For example, the size and/or function of the lung may be increased by at least 20%, at least 30%, at least 40%, at least 50%, at least 70%, at least 80%, at least 90%, at least 100%, at least 2-fold, at least 5-fold, at least 10-fold, at least 50-fold, at least 100-fold or more, in subjects that have been administered the fusion protein, compared to in subjects that have not been administered the fusion protein. In some embodiments, the size and/or function of the lung is increased by 20%, 30%, 40%, 50%, 70%, 80%, 90%, 100%, 2-fold, 5-fold, 10-fold, 50-fold, 100-fold or more, in subjects that have been administered the fusion protein, compared to in subjects that have not been administered the fusion protein.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Example 1. ApoM-Fc for Treating Bronchopulmonary Dysplasia

According to the Center for Disease Control and Prevention, preterm Birth affects 1 in 10 infants born in the United States. Of these preterm births, 8.8/1000 require extended medical ventilation with oxygen supplementation. Approximately 1 in 4 preterm infants on ventilation develop bronchopulmonary dysplasia (BPD), a clinical pathology that arises as a result of exposure to hyperoxia (high oxygen). Extended exposure to oxygen under these conditions results in destruction of the both the lung alveoli and vascular bed. Healthy lung structure is replaced by scar tissue and an infiltration of inflammatory cells, a pathology that is observed in patients with Chronic Obstructive Pulmonary Disease (COPD). The tissue destruction decreases normal oxygen delivery in the patient. The long-term consequences of this pathology include impaired subsequent childhood physical and mental development and a predisposition to subsequent risk factors including asthma, pulmonary hypertension, corpulmonae (right heart failure) and repeated lung infections (e.g., as described in Ehrenkranz R A, et al. Pediatrics 2005 December; 116(6):1353-60, incorporated herein by reference). The National Institutes of Health estimates that there are 10,00-15,000 new cases of BPD annually in the United States. While the addition of pulmonary surfactant as a treatment for lung development in preterm infants has decreased the severity of the hyperoxia-induced BPD, at present there is no therapeutic to either prevent or treat BPD.

An animal model has been developed for mice, which mimics the observable lung pathology of BPD (e.g., in Berger et al., Am J Physiol Lung Cell Mol Physiol, 307912: L936-47, 2014, incorporated herein by reference). The BPD animal model was used herein for testing the therapeutic effects of the ApoM-Fc fusion proteins. At birth, mouse pups were placed in a chamber that maintains an atmosphere of 90% oxygen. After 10 days mice were returned to normoxia (normal air) for at least 3 days. Histopathology of lung tissue reveals extensive destruction of alveoli, infiltration of inflammatory mononuclear cells and accumulation of pleural effusions (fluid). The observed pathology is consistent with both BPD observed in preterm infants and COPD (emphysema) observed in adults.

Figure 1B:
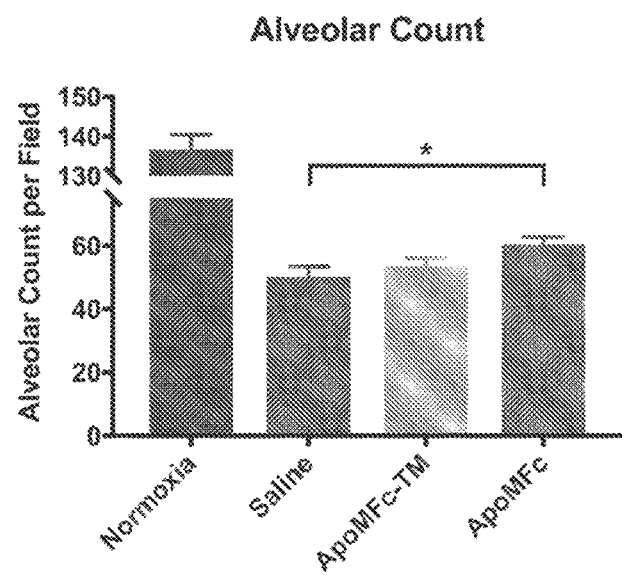

Next, ApoM-Fc (4 mg/Kg), ApoM-Fc-TM (4 mg/Kg), or saline control were tested in the animal model for BPD. Newborn (P1) pups were dosed on alternating days while being maintained in 90% oxygen and after ten days were returned to normoxia for 3 days. Lungs, heart, liver, kidney and intestines were harvested, fixed in formalin, embedded in paraffin and 20 micron sections were prepared and stained with Hematoxylin and Eosin. Microscopic analysis of lungs reveals that ApoM-Fc treatment decreases the severity of BPD, as indicated by the increased number of intact alveoli demonstrated by the histology shown in FIG. 1A. Quantification of the histological sections revealed a statistically significant (P=0.05) 20% increase in total number of preserved Alveoli (Alveolar Count) (FIG. 1B). These data suggest that ApoM-Fc are therapeutically effective in the treatment of BPD.

Example 2. ApoM-Fc for Treating Congenital Diaphragmatic Hernia

Congenital Diaphragmatic Hernia (CDH) is a lung malformation of the diaphragm that occurs with an incidence of 1:2000 births. During development, an incomplete closure of the diaphragm around the esophagus allows abdominal organs to enter the chest cavity resulting in compression of the left lung, most commonly, and occasionally the right lung. The resulting lung compression results in inhibition of lung development. At present the mortality rate in this disease is between 40-60%. The malformation is treated by surgical intervention around the time of birth. However, at present there is no therapeutic intervention for the stimulation of regrowth of the underdeveloped neonatal lung.

Figure 2A:
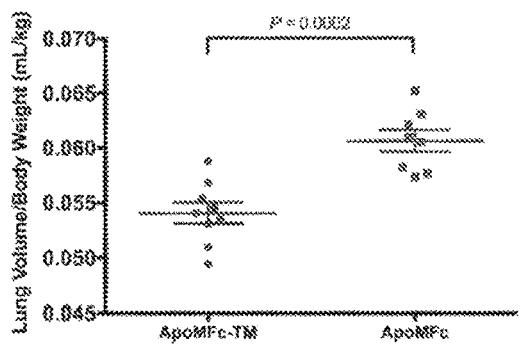
FIGS. 2A-2D. ApoM-Fc improves 4 parameters of lung regeneration in a partial pneumonectomy model for Congenital Diaphragmatic Hernia (CDH) induced lung development. Four days after partial pneumonectomy, lung function was evaluated using a Flexivent spirometer (Scireq), evaluating total lung tidal volume (FIG. 2A), Compliance (distendability.
Figure 2B:
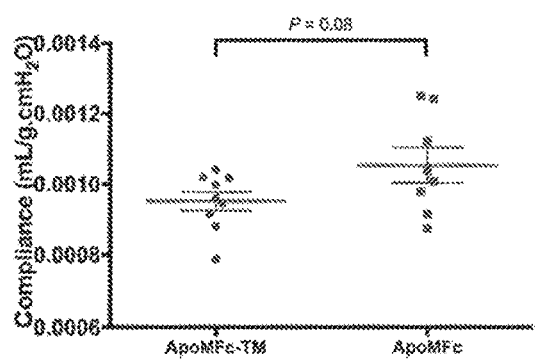
Figure 2C:
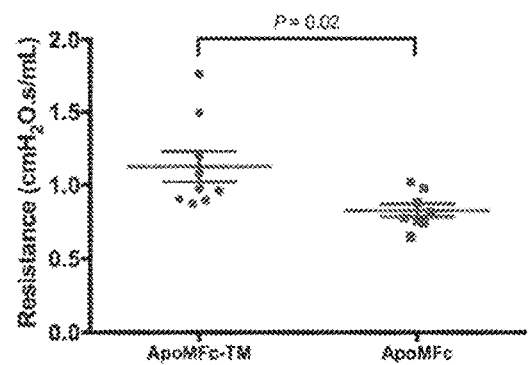
Figure 2D:
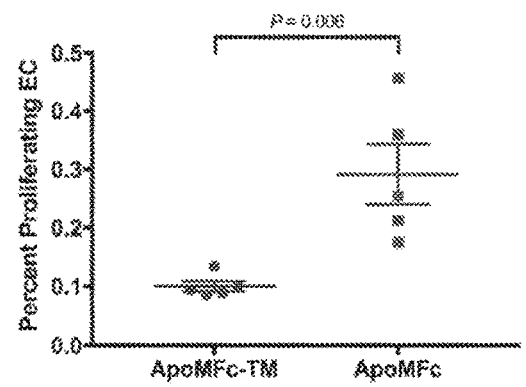

Partial pneumonectomy of the left lung in adult mammals has been established as model for CDH and for evaluating potential therapeutic approaches to lung regeneration[11]. The effects of ApoM-Fc as compared to controls in the lung regeneration model were evaluated. Following surgery, mice were given 1 dose of either ApoM-Fc or ApoM-Fc-TM (4 mg/Kg) and maintained for 4 days. On day 4, several parameters of lung function were evaluated and quantified using spirometry (FIGS. 2A-2C). Upon completion of the studies lungs were harvested and fixed and histological sections were prepared for immunofluorescence staining using the markers Ki-67 and CD31, to determine the proliferative response (reflecting lung regeneration). The immunofluorescence data of treated lung tissue was quantified (FIG. 2D). The combined data suggests that ApoM-Fc demonstrated statistically significant improvement in 4 parameters of lung function, consistent with increased lung regeneration (FIGS. 2A-2D).

Materials and Methods

Induction of BPD in C57Bl/6 and Treatment with ApoM-Fc

C57Bl/6 mouse pups (P1) were injected subcutaneously with either saline, ApoM-Fc (4 mg/kg) or the mutant non-functional ApoM-Fc-TM (4 mg/kg), as described previously (Swendeman S., et al. Sci Signal 2017 Aug. 15; 10(492), incorporated herein by reference). Mouse pups were then maintained in 90% oxygen for 10 days and dosed at 4 mg/kg for either protein on odd successive days until mice were returned to normoxia on day 10 post-birth. Mice were then sacrificed at day 13.

Histological Analysis of Mouse Tissues

Heart, Lung Liver, kidney and intestines were harvested from each mouse and fixed in 10% formalin. Formalin fixed tissues were embedded in paraffin, 20 micron sections were cut on a microtome and mounted for staining by Hematoxylin and Eosin. Analysis of histological sections revealed a marked protection of alveoli structure and a decrease in inflammatory mononuclear cells infiltration in mice treated with ApoM-Fc. (FIGS. 1A-1B).

Partial Pneumonectomy in Adult Mice and Treatment with ApoM-Fc

WT C57Bl/6 mice were subjected to surgical partial left-lung pneumonectomy and were treated with either saline (control; not shown) or 1 dose of 4 mg/Kg of either ApoM-Fc-TM (negative control) or ApoM-Fc according IACUC standards. Four days after partial pneumonectomy, lung function was evaluated using a Flexivent spirometer (Scireq) using manufacturer's suggested parameters. Following measurements, lung tissue was harvested, embedded in OCT and sectioned while frozen. Sections were stained by standard immunohistochemical methods using monoclonal antibodies to the proliferation marker Ki-67 (Abcam; ab15580) and CD31 (R&D Systems; AF3628-SP) and appropriate secondary antiserum. Slides were visualized by fluorescent microscopy and photographed. 5 microscopic fields were evaluated per slide and double staining cells were counted in a blinded manner.

TABLE 1

Mouse and Human ApoM, Fc (IgG1 constant region) and ApoM-Fc fusion protein Sequences

| Name | Sequence | SEQ ID NO: |
|---|---|---|
| Domain Sequences | | |
| Human ApoM | YQCPEHSQLTTLGVDGKEFPEVHLGQWYFIAGAAPTKEELATFDP VDNIVFNMAAGSAPMQLHLRATIRMKDGLCVPRKWIYHLTEGST DLRTEGRPDMKTELFSSSCPGGIMLNETGQGYQRFLLYNRSPHPP EKCVEEFKSLTSCLDSKAFLLTPRNQEACELSNN | 5 |
| Mouse ApoM | NQCPEHSQLTALGMDDTETPEPHLGLWYFIAGAAPTEELATFDP VDNIVFNMAAGSAPRQLQLRATIRTKSGVCVPRKWTYRLTEGKG NMELRTEGRPDMKTDLFSSSCPGGIMLKETGQGYQRFLLYNRSP HPPEKCVEEFKSLTSCLDFKAFLVTPRNQEACPLSSK | 6 |
| Human IgG1Fc | WASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPELLGGPSVFLFPPKPKDTLM ISRTPEVTCVVVDVSHEDPEVKFNWYVDGVEVHNAKTKPREEQY NSTYRVVSVLTVLHQDWLNGKEYKCKVSNKALPAPIEKTISKAK GQPREPQVYTLPPSREEMTKNQVSLTCLVKGFYPSDIAVEWESNG QPENNYKTTPPVLDSDGSFFLYSKLTVDKSRWQQGNVFSCSVMH EALHNHYTQKSLSLSPGK | 7 |
| Mouse IgG1Fc | WISSASSAKTTPPSVYPLAPGSAAQTNSMVTLGCLVKGYFPEPVT VTWNSGSLSSGVHTFPAVLQSDLYTLSSSVTVPSSTWPSETVTCN VAHPASSTKVDKKIVPRDCGCKPCICTVPEVSSVFIFPPKPKDVLTI TLTPKVTCVVVDISKDDPEVQFSWFVDDVEVHTAQTQPREEQFN STFRSVSELPIMHQDWLNGKEFKCRVNSAAFPAPIEKTISKTKGRP KAPQVYTIPPPKEQMAKDKVSLTCMITDFFPEDITVEWQWNGQP AENYKNTQPIMDTDGSYFVYSKLNVQKSNWEAGNTFTCSVLHE GLHNHHTEKSLSHSPGK | 8 |
| Fusion protein Sequences | | |
| Amino acid sequence of Human ApoM-human IgG1Fc Fusion (hApoM-Fc) | MYRMQLLSCIALSLALVTNSISRVYQCPEHSQLTTLGVDGKEFP EVHLGQWYFIAGAAPTKEELATFDPVDNIVFNMAAGSAPMQL HLRATIRMKDGLCVPRKWIYHLTEGSTDLRTEGRPDMKTEL FSSSCPGGIMLNETGQGYQRFLLYNRSPHPPEKCVEEFKSLTS CLDSKAELLTPRNQEACELSNN*WASTKGPSVFPLAPSSKSTSGGTA ALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVE VHNAKTKPREEQYNSTYRVVSVLTVLHQDWLNGKEYKCKVSNKALPA PIEKTISKAKGQPREPQVYTLPPSREEMTKNQVSLTCLVKGFYPSDIAV EWESNGQPENNYKTTPPVLDSDGSFFLYSKLTVDKSRWQQGNVFSCS VMHEALHNHYTQKSLSLSPGK** | 1 |
| Amino acid sequence of Mouse ApoM-mouse IgG1Fc fusion (mApoM-Fc) | MYRMQLLSCIALSLALVTNSNQCPEHSQLTALGMDDTETPEPH LGLWYFIAGAAPTEELATFDPVDNIVFNMAAGSAPRQLQLR ATIRTKSGVCVPRKWTYRLTEGKGNMELRTEGRPDMKTDLF SSSCPGGIMLKETGQGYQRFLLYNRSPHPPEKCVEEFKSLTSC LDFKAFLVTPRNQEACPLSSK*WISSASSAKTTPPSVYPLAPGSAAQT NSMVTLGCLVKGYFPEPVTVTWNSGSLSSGVHTFPAVLQSDLYTLSSS VTVPSSTWPSETVTCNVAHPASSTKVDKKIVPRDCGCKPCICTVPEVSS VFIFPPKPKDVLTITLTPKVTCVVVDISKDDPEVQFSWFVDDVEVHTA QTQPREEQFNSTFRSVSELPIMHQDWLNGKEFKCRVNSAAFPAPIEK TISKTKGRPKAPQVYTIPPPKEQMAKDKVSLTCMITDFFPEDITVEWQ WNGQPAENYKNTQPIMDTDGSYFVYSKLNVQKSNWEAGNTFTCSVL HEGLHNHHTEKSLSHSPGK** | 2 |
| Amino acid sequence of human ApoM-mouse IgG1Fc fusion | MYRMQLLSCIALSLALVTNSISRVYQCPEHSQLTTLGVDGKEFP EVHLGQWYFIAGAAPTKEELATFDPVDNIVFNMAAGSAPMQL HLRATIRMKDGLCVPRKWIYHLTEGSTDLRTEGRPDMKTEL FSSSCPGGIMLNETGQGYQRFLLYNRSPHPPEKCVEEFKSLTS CLDSKAFLLTPRNQEACELSNN*WISSASSAKTTPPSVYPLAPGSAA QTNSMVTLGCLVKGYFPEPVTVTWNSGSLSSGVHTFPAVLQSDLYTLS SSVTVPSSTWPSETVTCNVAHPASSTKVDKKIVPRDCGCKPCICTVPEV SSVFIFPPKPKDVLTITLTPKVTCVVVDISKDDPEVQFSWFVDDVEVH TAQTQPREEQFNSTFRSVSELPIMHQDWLNGKEFKCRVNSAAFPAPI EKTISKTKGRPKAPQVYTIPPPKEQMAKDKVSLTCMITDFFPEDITVE WQWNGQPAENYKNTQPIMDTDGSYFVYSKLNVQKSNWEAGNTFTCS VLHEGLHNHHTEKSLSHSPGK** | 3 |
| Amino acid sequence of mouse ApoM- | MYRMQLLSCIALSLALVTNSNQCPEHSQLTALGMDDTETPEPH LGLWYFIAGAAPTEELATFDPVDNIVFNMAAGSAPRQLQLR | 4 |

TABLE 1-continued

Mouse and Human ApoM, Fc (IgG1 constant region) and ApoM-Fc fusion protein Sequences

| Name | Sequence | SEQ ID NO: |
|---|---|---|
| human IgG1Fc fusion (mApoM-hFc) | ATIRTKSGVCVPRKWTYRLTEGKGNMELRTEGRPDMKTDLF SSSCPGGIMLKETGQGYQRFLLYNRSPHPPEKCVEEFKSLTSC LDFKAFLVTPRNQEACPLSSKWASTKGPSVFPLAPSSKSTSGGTAA LGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGG PSVFLFPPKPKDTLMISRTPEVTCVVVDVSHEDPEVKFNWYVDGVEV HNAKTKPREEQYNSTYRVVSVLTVLHQDWLNGKEYKCKVSNKALPAP IEKTISKAKGQPREPQVYTLPPSREEMTKNQVSLTCLVKGFYPSDIAVE WESNGQPENNYKTTPPVLDSDGSFFLYSKLTVDKSRWQQGNVFSCSV MHEALHNHYTQKSLSLSPGK* | |
| Amino acid sequence of Mouse ApoM-mouse IgG1Fc-His6 fusion (mApoM-mFc) | MYRMQLLSCIALSLALVTNSNQCPEHSQLTALGMDDTETPEPH LGLWYFIAGAAPTTEELATFDPVDNIVFNMAAGSAPRQLQLR ATIRTKSGVCVPRKWTYRLTEGKGNMELRTEGRPDMKTDLF SSSCPGGIMLKETGQGYQRFLLYNRSPHPPEKCVEEFKSLTSC LDFKAFLVTPRNQEACPLSSKWISSASSAKTTPPSVYPLAPGSAAQT NSMVTLGCLVKGYFPEPVTVTWNSGSLSSGVHTFPAVLQSDLYTLSSS VTVPSSTWPSETVTCNVAHPASSTKVDKKIVPRDCGCKPCICTVPEVSS VFIFPPKPKDVLTITLTPKVTCVVVDISKDDPEVQFSWFVDDVEVHTA QTQPREEQFNSTFRSVSELPIMHQDWLNGKEFKCRVNSAAFPAPIEK TISKTKGRPKAPQVYTIPPPKEQMAKDKVSLTCMITDFFPEDITVEWQ WNGQPQENYKNTQPIMDTDGSYFVYSKLNVQKSNWEAGNTFTCSVL HEGLHNHHTEKSLSHSPGKHHHHHH* | 9 |
| Nucleotide Sequences Encoding the Fusion Proteins | | |
| Polynucleotide sequence of Murine ApoM-mouse IgG1 Fc Fusion (mApoM-mFc) | *Atg*tacaggatgcaactcctgtcttgcattgcactaagtcttgcacttgtcacgaattcg**aatcagtgccc tgagcacagtcaactaactgcgctgggaatggacgacacagagaccccagagcccacctggg cctgtggtactttattgcgggagcagcccccaccacggaagagttggcaactttgatccggtgga caatattgtcttcaacatggctgccggctctgccccaaggcagctccagcttcgtgctaccatccgc acgaaaagtgggg tctgtgtgccccgaagtggacataccgattgactgaagggaaaggaaac atggaactcagaactgaagggcgcccagacatgaaaacagacctgttctccagctcgtgcccag gaggaatcatgctgaaagagacgggccagggctaccagcgctttctcctctacaatcggtcacca caccctccagagaagtgtgtggaggaattcaagtctctgacctcttgcttggacttcaaagccttct tagtgactcccaggaatcaagaggcctgccgctgtccagcaagtgga*tatcgagt*gctagcagcg ctaaaacgacaccccca tctgtctatccactggcccctggatctgctgcccaaactaactccatggtgac cctgggatgcctggtcaagggctatttccctgagccagtgacagtgacctggaactctggatccctgtcc agcggtgtgcacacctt cccagctgtcctgcagtctgacctctacactctgagcagctcagtgactgtcc cctccagcacctggccagcgagaccgtcacctgcaacgttgcccaccggccagcagccaccaaggt ggacaagaaaattgtgcccagggattgtggttgtaagccttgcatatgtacagtcccagaagtatcatctg tcttcatcttccccccaaagcccaaggatgtgctcaccattactctgactcctaaggtcacgtgtgttgtggt agacatcagcaaggatgatcccgaggtccagttcagctggtttgtagatgatgtggaggtgcacacagc tcagacgcaacccggagggaggagttcaacagcacttttccgctcagtcagtgaacttccca tcatgca ccaggactggctcaatggcaaggagttcaaatgcagggtcaacagtgcagctttccctgcccccatcga gaaaaccatctccaaaaccaaaggcagaccgaaggctccgcaggtgtacaccattccacctcccaag gagcagatggccaaggataaagtcagtctgacctgcatgataacagacttcttccctgaagacattactg tggagtggcagtggaatgggcagccagcggagaactacaagaacactcagcccatcatggacacag atggctcttacttcgtctacagcaagctcaatgtgcagaagagcaactgggaggcaggaaatactttcac ctgctctgtgttacatgagggcctgcacaaccaccatactgagaagagcctctcccactctcctggtaaa*t ga* | 10 |
| Polynucleotide sequence of Human ApoM-human IgG1Fc Fusion (hApoM-hFc) | *Atg*tacaggatgcaactcctgtcttgcattgcactaagtcttgcacttgtcacgaattcgata*tctcgagtgt* accagtgccctgagcacagtcaactgacaactctgggcgtggatgggaaggagttcccagaggt ccactgggccagtggtactttatcgcaggggcagctccaccaaggaggagttggcaactttg acc ctgtggacaacattgtcttcaatatggctgctggctctgccccgatgcagctccaccttcgtgct accatccgcatgaaagatgggctctgtgtgccccgg aaatggatctaccacctgactgaaggga gcacagatctcagaactgaaggccgccctgacatgaagactgagctcttttccagctcatgccca ggtggaatcatgctgaatgagacaggccagggtaccagcgctttctcctctacaatcgctcacca catcctcccgaaagtgtgtggaggaattcaagtccctgacttcctgcctggactccaaagccttct tattgactcctaggaatcaagaggcctgtgagctgtccaataact*gggctagc*accaaggccca t cggtcttcccctggcacccctcctccaagagcacctctgggggcacagcggccctgggctgcctggtc aaggactacttccccgaaccggtgacggtgtcgtggaactcaggcgccctgaccagcggcgtgcaca ccttcccggctgtcctacagtcctcaggactctactccctcagcagcgtggtgaccgtgccctccagcag cttgggcacccagacctacatctgcaacgtgaatcacaagcccagcaacaccaaggtggacaagaaa gttgagcccaaatcttgtgacaaaactcacacatgcccaccgtgcccagcacctgaactcctggggga ccgtcagtcttcctcttccccccaaaacccaaggacaccctcatgatctcccggacccctgaggtcacat gcgtggtggtggacgtgagccacgaagaccctgaggtcaagttcaactggtacgtggacggcgtgga ggtgcataatgccaagacaaagccgcgggaggagcagtacaacagcacgtaccgtgtggtcagcgtc ctcaccgtcctgcaccaggactggctgaatggcaaggagtacaagtgcaaggtctccaacaaagccct cccagcccccatcgagaaaaccatctccaaagccaaagggcagccccgagaaccacaggtgtacac cctgcccccatcccgggaggagatgaccaagaaccaggtcagcctgacctgcctggtcaaaggcttct atcccagcgacatcgccgtggagtgggagagcaatgggcagccggagaacaactacaagaccacgc ctcccgtgctggactccgacggctccttcttcctctacagcaagctcaccgtggacaagagcaggtggc** | 11 |

TABLE 1-continued

Mouse and Human ApoM, Fc (IgG1 constant region) and ApoM-Fc fusion protein Sequences

| Name | Sequence | SEQ ID NO: |
|---|---|---|
| | agcagggggaacgtcttctcatgctccgtgatgcatgaggctctgcacaaccactacacgcagaagagc ctctccctgtctccgggtaaatga | |
| Polynucleotide sequence of Human ApoM-mouse IgG1Fc Fusion (hApoM-mFc) | Atgtacaggatgcaactcctgtcttgcattgcactaagtcttgcacttgtcacgaattcgatatctcgagtgt accagtgccctgagcacagtcaactgacaactctgggcgtggatgggaaggagttcccagaggt ccacttgggccagtggtactttatcgcaggggcagctcccaccaaggaggagttggcaacttttg accctgtggacaacattgtcttcaatatggctgctggctctgccccgatgcagctccaccttcgtgct accatccgcatgaaagatgggctctgtgtgccccggaaatggatctaccacctgactgaaggga gcacagatctcagaactgaaggccgcccctgacatgaagactgagctcttttccagctcatgccca ggtggaatcatgctgaatgagacaggccagggttaccagcgctttctcctctacaatcgctcacca catcctcccgaaaagtgtgtggaggaattcaagtccctgacttcctgcctggactccaaagccttct tattgactcccaggaatcaagaggcctgtgagctgtccaataactggatctcgagtgctagcagcgc taaaacgacacccccatctgtctatccactggcccctggatctgctgcccaaactaactccatggtgacc ctgggatgcctggtcaagggctatttccctgagccagtgacagtgacctggaactctggatccctgtcca gcggtgtgcacaccttcccagctgtcctgcagtctgacctctacactctgagcagctcagtgactgtccc ctccagcacctggcccagcgagaccgtcacctgcaacgttgcccacccggccagcagcaccaaggtg gacaagaaaattgtgcccagggattgtggttgtaagccttgcatatgtacagtcccagaagtatcatctgt ctttcatcttcccccaaagcccaaggatgtgctcaccattactctgactcctaaggtcacgtgtgttgtggt agacatcagcaaggatgatcccgaggtccagttcagctggttttgtagatgatgtggaggtgcacacagc tcagacgcaaccccgggaggagcagttcaacagcactttccgctcagtcagtgaacttcccatcatgca ccaggactggctcaatggcaaggagttcaaatgcagggtcaacagtgcagctttccctgccccatcga gaaaccatctccaaaaccaaaggcagaccgaaggctccgcaggtgtacaccattccacctcccaag gagcagatggccaaggataaagtcagtctgacctgcatgataacagacttcttccctgaagacattactg tggagtggcagtggaatgggcagcagcggagaactacaagaacactcagcccatcatggacaag atggctcttactcgtctacagcaagctcaatgtgcagaagagcaactgggaggcaggaaatactttcac ctgctctctgttgtacatgagggcctgcacaaccaccatactgagaagagcctctcccactctcctggtaaat ga | 12 |
| Polynucleotide sequence of mouse ApoM-human IgG1Fc Fusion (mApoM-hFc) | Atgtacaggatgcaactcctgtcttgcattgcactaagtcttgcacttgtcacgaattcgaatcagtgccc tgagcacagtcaactaactgcgctgggaatggacgacacagagaccccagagcccacctggg cctgtggtactttattgcggggagcagccccccaccacggaagagttggcaacttttgatccggtgga caatattgtcttcaacatggctgccggctctgccccaaggcagctccagcttcgtgctaccatccgc acgaaagtggggtctgtgtgccccggaagtggacataccgattgactgaagggaaaggaaac atggaactcagaactgaagggcgcccagacatgaaaacagacctgttctccagctcgtgcccag gaggaatcatgctgaaagagacgggccagggctaccagcgcttctcctctacaatcggtcacca caccctccagagaagtgtgtggaggaattcaagtctctgacctcttgcttggacttcaaagccttct tagtgactcccaggaatcaagaggcctgccgctgtccagcaagtggctagcaccaagggccca tcggtcttcccctggcacccctcctccaagagcacctctggggcacagcggccctgggctgcctggt caaggactacttccccgaaccggtgacggtgtcgtggaactcaggcgccctgaccagcggcgtgcac accttcccggctgtcctacagtcctcaggactctactccctcagcagcgtggtgaccgtgccctccagca gcttgggcacccagacctacatctgcaacgtgaatcacaagcccagcaacaccaaggtggacaagaa agttgagcccaaatcttgtgacaaaactcacacatgcccaccgtgcccagcacctgaactcctgggggga accgtcagtcttcctcttcccccaaaacccaaggacaccctcatgatctcccggacccctgaggtcaca tgcgtggtggtggacgtgagccacgaagaccctgaggtcaagttcaactggtacgtggacggcgtgga ggtgcataatgccaagacaaagccgcggggaggagcagtacaacagcacgtaccgtgtggtcagcgtc ctcaccgtcctgcaccaggactggctgaatggcaaggagtacaagtgcaaggtctccaacaaagccct cccagcccccatcgagaaaaccatctccaaagccaaagggcagccccgagaaccacaggtgtacac cctgcccccatcccgggaggagatgaccaagaaccaggtcagcctgacctgcctggtcaaaggcttct atcccagcgacatcgccgtggagtgggagagcaatgggcagccggagaacaactacaagaccacg cctcccgtgctggactccgacggctccttcttcctctacagcaagctcaccgtggacaagagcaggtggc agcaggggaacgtcttctcatgctccgtgatgcatgaggctctgcacaaccactacacgcagaagagc ctctccctgtctccgggtaaatga | 13 |
| Polynucleotide sequence of murine ApoM-mouseIgG1Fc-His Fusion (mApoM-mFc-His) | Atgtacaggatgcaactcctgtcttgcattgcactaagtcttgcacttgtcacgaattcgaatcagtgccc tgagcacagtcaactaactgcgctgggaatggacgacacagagaccccagagcccacctggg cctgtggtactttattgcggggagcagccccccaccacggaagagttggcaacttttgatccggtgga caatattgtcttcaacatggctgccggctctgccccaaggcagctccagcttcgtgctaccatccgc acgaaagtggggtctgtgtgccccggaagtggacataccgattgactgaagggaaaggaaac atggaactcagaactgaagggcgcccagacatgaaaacagacctgttctccagctcgtgcccag gaggaatcatgctgaaagagacgggccagggctaccagcgcttctcctctacaatcggtcacca caccctccagagaagtgtgtggaggaattcaagtctctgacctcttgcttggacttcaaagccttct tagtgactcccaggaatcaagaggcctgccgctgtccagcaagtggatctcgagtgctagcagcg ctaaaacgacacccccatctgtctatccactggcccctggatctgctgcccaaactaactccatggtgac cctgggatgcctggtcaagggctatttccctgagccagtgacagtgacctggaactctggatccctgtcc agcggtgtgcacaccttcccagctgtcctgcagtctgacctctacactctgagcagctcagtgactgtccc ctccagcacctggcccagcgagaccgtcacctgcaacgttgcccacccggccagcagcaccaaggt ggacaagaaaattgtgcccagggattgtggttgtaagccttgcatatgtacagtcccagaagtatcatctg tctttcatcttcccccaaagcccaaggatgtgctcaccattactctgactcctaaggtcacgtgtgttgtggt agacatcagcaaggatgatcccgaggtccagttcagctggttttgtagatgatgtggaggtgcacacagc tcagacgcaaccccgggaggagcagttcaacagcactttccgctcagtcagtgaacttcccatcatgca ccaggactggctcaatggcaaggagttcaaatgcagggtcaacagtgcagctttccctgccccatcga gaaaccatctccaaaaccaaaggcagaccgaaggctccgcaggtgtacaccattccacctcccaag gagcagatggccaaggataaagtcagtctgacctgcatgataacagacttcttccctgaagacattactg | 14 |

TABLE 1-continued

Mouse and Human ApoM, Fc (IgG1 constant region) and ApoM-Fc fusion protein Sequences

| Name | Sequence | SEQ ID NO: |
|---|---|---|
| | tggagtggcagtggaatgggcagccagcggagaactacaagaacactcagcccatcatggacacag atggctcttacttcgtctacagcaagctcaatgtgcagaagagcaactgggaggcaggaaatactttcac ctgctctgtgttacatgagggcctgcacaaccaccatactgagaagagcctctcccactctcctggtaaa catcaccatcaccatcactga | |

Example 3. Analysis of ApoM-Fc-S1P Complexes

Figure 3:
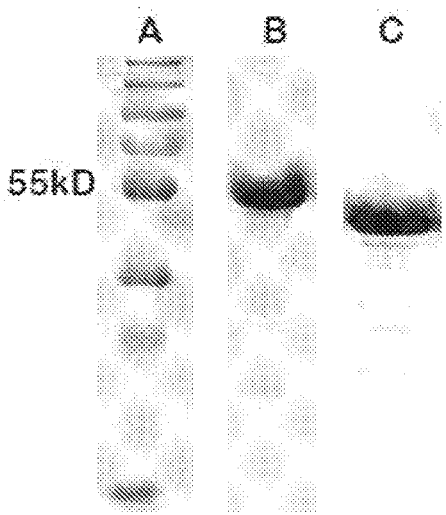
FIG. 3. Purification of human and mouse ApoM-IgG1 Fc proteins to homogeneity. Lane A: PageRuler Plus Prestained Protein Ladder (ThermoFisher; Range 250-10 kD); 55 kD is identified. Lane B: hApoM-Fc (6 µg). Lane C: mApoM-Fc (6 µg).

The recombinant human-human and mouse-mouse ApoM-Fc fusion proteins were expressed to homogeneity (FIG. 3). In order to function as an active biologic, human or mouse ApoM-Fc were loaded with the lipid S1P.

Second, bioactivity towards sphingosine 1-phosphate receptor-1 (S1PR1) were determined by demonstrating that ApoM-Fc-S1P complex potently activates the S1PR1-coupled $G_i$ activity and S1PR1-coupled ß-arrestin coupling. The S1P receptors are members of the G-protein coupled receptor (GPCR) superfamily. Receptor activation is characterized by immediate activation of a G-protein complex (alpha-beta-gamma) that activates multiple intracellular signaling pathways and then secondary activation of coupling to the protein beta-arrestin, which may cause receptor internalization and desensitization as well as activation of other intracellular signaling pathways. Inoue et al (Cell. 2019 Jun. 13; 177(7):1933-1947) established a split luciferase assay that allows for rapid analysis of either G-Protein coupling or beta-arrestin binding to a given receptor. Luciferase is split in to "Large bit" and "Small Bit" domains which are fused to various protein partners and may be rejoined into functional luciferase upon dimerization of the partners.

Figure 5A:
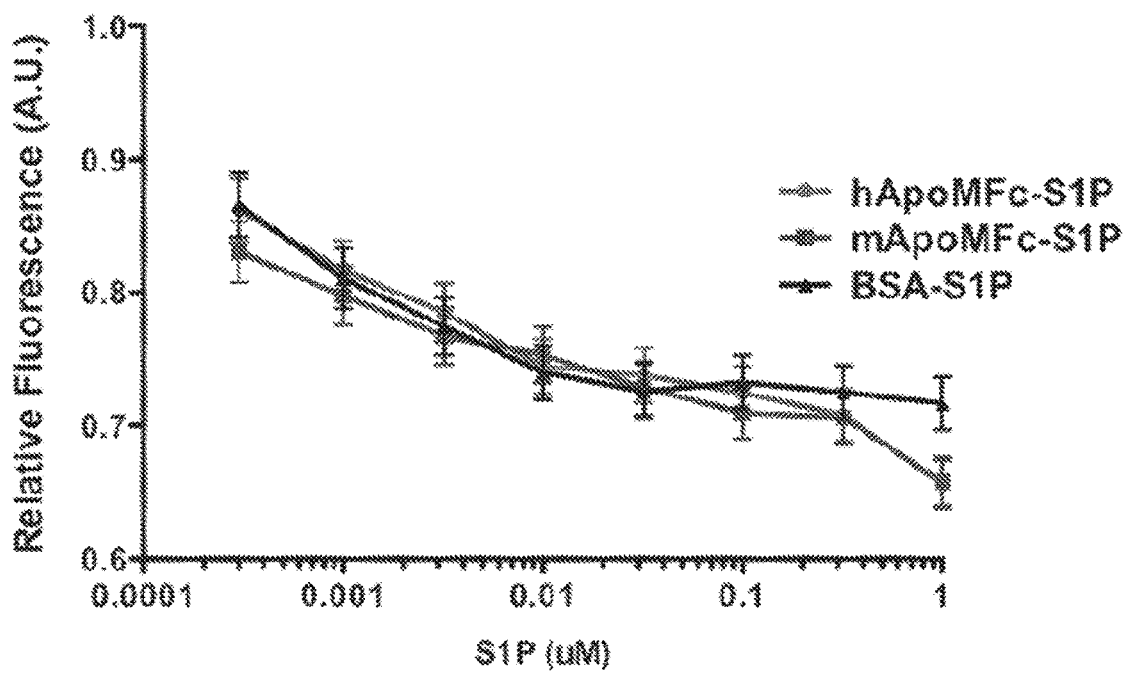
FIGS. 5A-5B. Nanobit analysis of Human ApoMFc-S1P, Mouse ApoMFc-S1P, or BSA-S1P (Positive Control). Human ApoMFc-S1P, Mouse ApoMFc-S1P, or BSA-S1P (Positive Control) equivalently activates Gi-alpha Coupling (FIG. 5A) and beta-arrestin coupling (FIG. 5B) to the S1P1 receptor. BSA-S1P is the well-established activator of the S1PR1 and it was tested whether Human ApoMFc-S1P, Mouse ApoMFc-S1P gave equivalent induction of receptor activation. Data are the means of triplicate wells with the baseline (pre-stimulation) signal subtracted from the final luciferase signal and graphs are expressed with standard deviation.
Figure 5B:
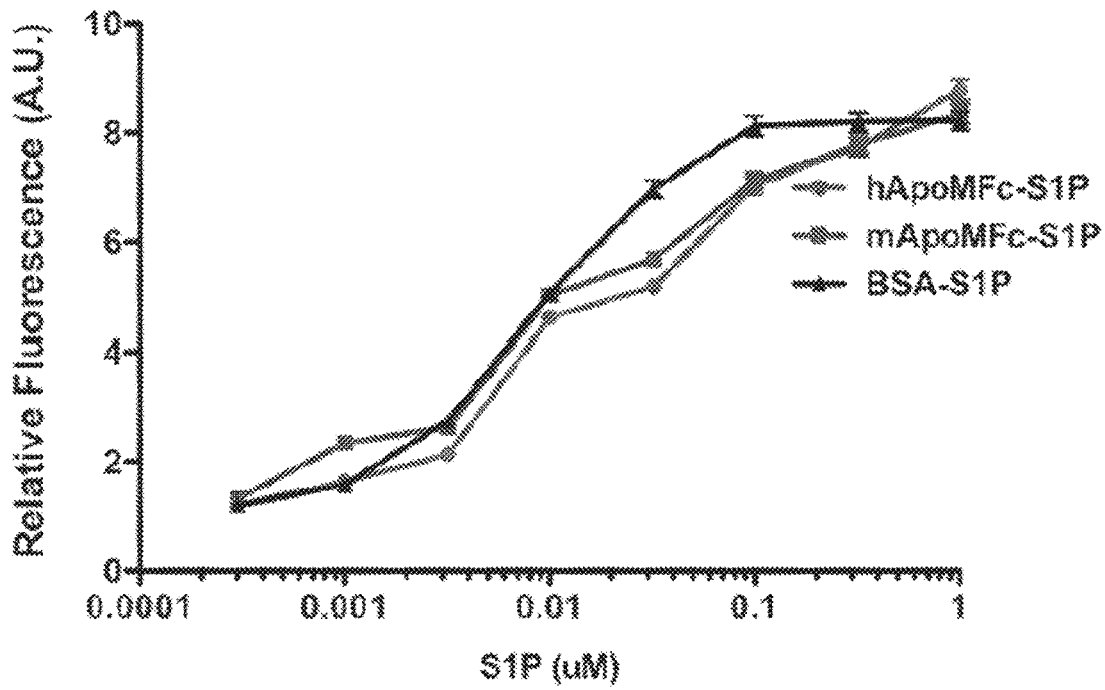

There are two general forms of this assay. In the G-Protein assay a given GPCR-expressing mammalian expression plasmid is co-transfected with three other plasmids expressing G-alpha-Large bit luciferase, G-beta, and G-gamma (Small bit). Upon activation of the GPCR, the G-Protein alpha-beta-gamma complex is formed and Luciferase activity may be detected by measuring emitted light in the presence of luciferase substrate (luciferin). In the alternate form of the assay, the GPCR is fused to the "small bit" of luciferase and co-transfected with beta-arrestin-large bit. Again, upon activation, the GPCR-ß-arrestin complex reunites to generate luciferase activity. It is notable that G-Protein assay results in decreased relative fluorescence with increased receptor activation, while the Beta-arrestin coupling assay results in increased relative fluorescence with increased receptor activation. The results showed that Human ApoMFc-S1P, Mouse ApoMFc-S1P, or BSA-S1P (Positive Control) equivalently activates Gi-alpha Coupling and beta-arrestin coupling to the S1P1 receptor (FIGS. 5A and 5B).

Figure 4:
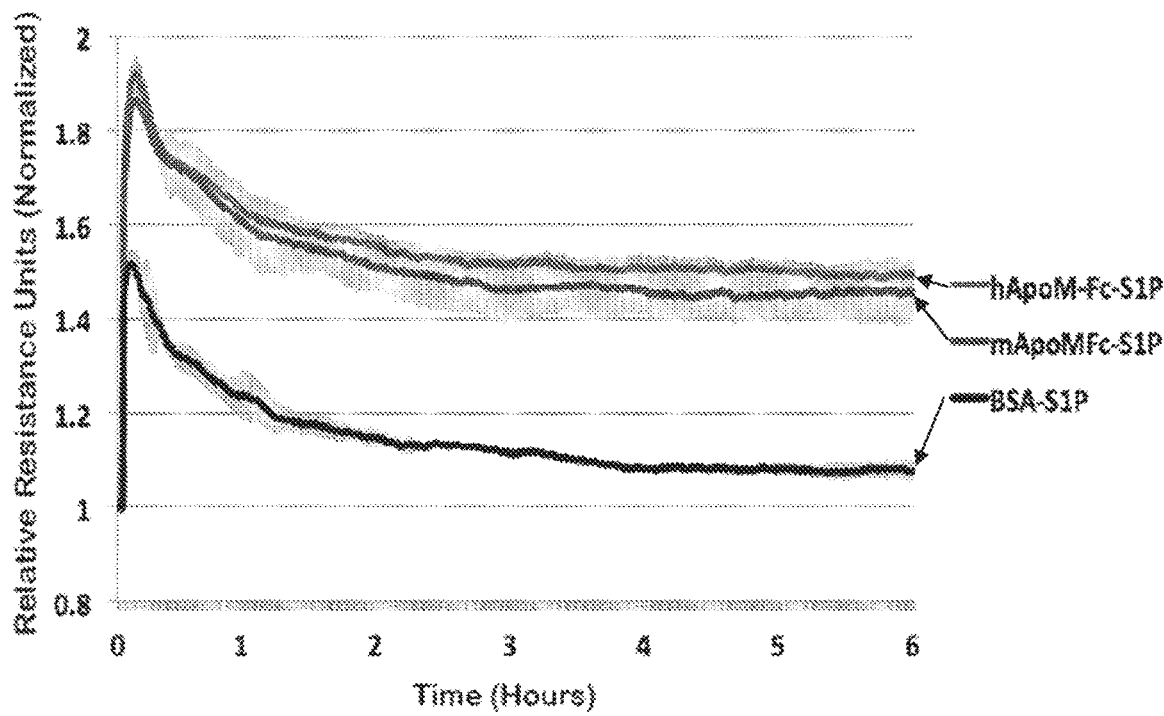
FIG. 4. Human and Mouse ApoM-Fc-S1P enhanced endothelial Barrier Protection. Human ApoMFc-S1P (4 µg/well, 250 nM S1P), Mouse ApoMFc-S1P (4 µg/well, 250 nM S1P), or BSA-S1P (250 nM S1P; Positive Control) were analyzed using transepithelial/transendothelial electrical resistance (TEER). The results of TEER analysis of HUVECs at the 6 hour time point are shown. BSA-S1P is the well-established activator of the S1PR1 and it was tested whether Human ApoMFc-S1P, Mouse ApoMFc-S1P gave equivalent induction of receptor activation. All results are normalized to individual well baselines (baseline=1), expressed as the mean of triplicate wells, and Standard Deviation (S.D.) is expressed as gray vertical bars over the course of the data set.

Third, the ability of ApoM-Fc-S1P complex to induce vascular barrier function was demonstrated by their activities on trans endothelial electrical resistance (TEER) assay. The TEER method is an established technique for evaluating the effect of a drug or biologic on the function of endothelial cell-cell junctions (endothelial barriers). It was established that ApoM-Fc-S1P strengthens endothelial barriers in vitro as described in (Swendeman et al, Sci Sig 2017 10:492) and this method is a useful evaluation of either hApoMFc-S1P or mApoMFc-S1P function on endothelial cells. The results indicated that Human and Mouse ApoM-Fc-S1P enhance endothelial Barrier Protection (FIG. 4).

Figure 6:
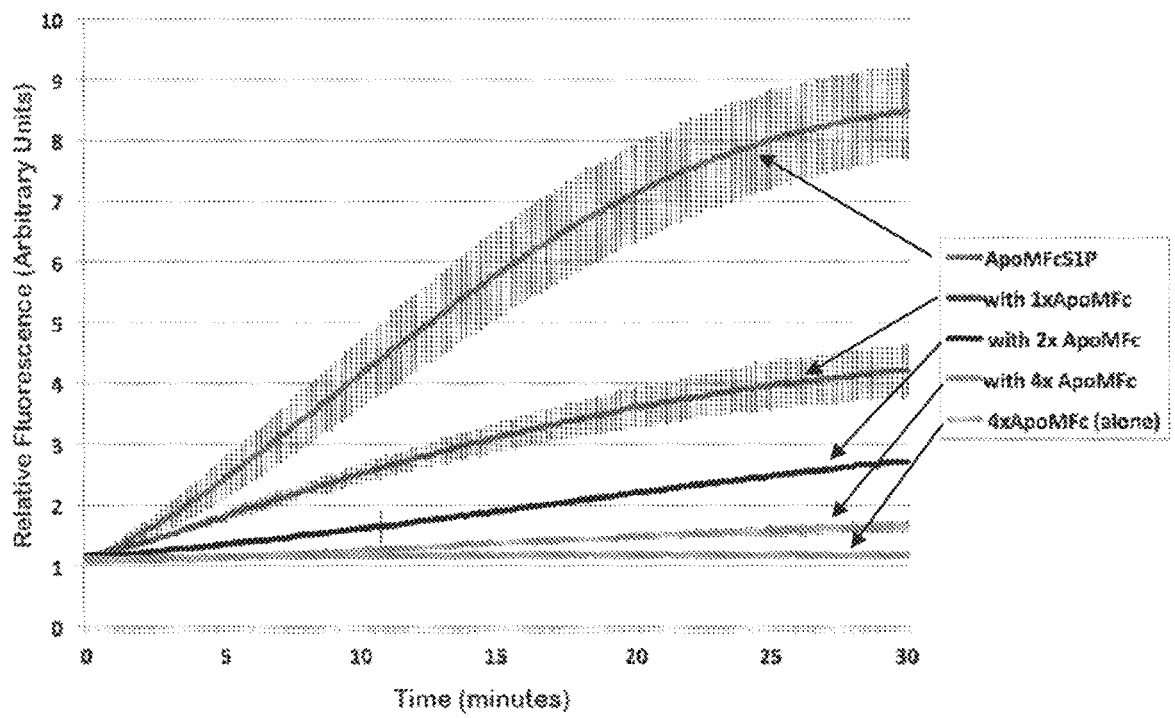
FIG. 6. ApoM-Fc can block ApoM-Fc-S1P dependent beta-arrestin coupling with S1P1. 4 µg of ApoMFc-S1P (250 nM S1P) was assayed alone or in combination with 4, 8, or 16 µg of ApoM-Fc, or 16 µg of ApoM-Fc was assayed alone. Data are the means of triplicate wells with the baseline (pre-stimulation) signal subtracted from the final luciferase signal and graphs are expressed with standard deviation.

Finally, the ability of nascent ApoM-Fc fusion proteins to block receptor activation and act as S1P) sponges were demonstrated by the competition assay on the Nanobit receptor signaling assay. An additional assay was created, employing the nanobit assay in combination with a mixture of both ApoM-Fc-S1P and ApoM-Fc (no S1P) to determine if empty ApoM-Fc could block ApoM-Fc-S1P dependent signaling in S1P1. The results of this assay suggests that ApoM-Fc and all mutants proposed in the patent could be assayed as functional blocking biologics for S1P) receptor activation (FIG. 6).

Methods

Loading Human ApoM-Human IgG1 Fc (hApoM-Fc) or Mouse ApoM-mouseIgG1Fc Fusion (mApoM-Fc) with S1P to Create hApoMFc-S1P or mApoMFC-S1P and In Vitro Analysis of Biological Function.

Purified hApoMFc or mApoMFc equilibrated in PBS were mixed with dried Sphingosine-1-Phosphate (S1P; Avanti Polar Lipids, Inc) at a molar ratio of (8:1; Lipid: Protein) by bath sonication. Samples were incubated overnight at 4° C. on a rotator. Protein-bound S1P) was separated from unbound lipid by FPLC Chromatography using paired Superose 6 10/300 GL size exclusion columns (GE Biosciences) and collected in 1 ml OD 280 positive fractions. Samples were concentrated on Amicon Ultra-4 Spin columns and suspended to a concentration of 1 mg/ml in Phosphate Buffered Saline.

Analysis of Human ApoM-IgG1 Fc (hApoM-Fc) and Mouse ApoM-IgG1Fc (mApoM-Fc-S1P) by Trans-Endothelial Electrical Resistance (TEER)

0.1 ml of Human Umbilical Vascular Endothelial Cells (HUVECS; 200,000 cells/ml in EGM-2 culture medium, Lonza) were seeded into a 96 well electrical conductance chamber (ECIS Cultureware; Applied Biophysics, Inc) pre-coated with 1% Fibronectin resuspended in Saline. After overnight incubation at 37° C./5% CO2, the 96-well plate was placed on the ECIS reader (Applied Biophysics; Ztheta 96-well array station) and baseline resistance was established which represents the quality of Endothelial junction strength or Endothelial barrier function. Medium was drawn off and replaced with M199 medium supplemented with 0.1% Bovine Serum Albumin (BSA) to serum starve and reduce background signaling. Samples to be tested were suspended in M199/0.1% BSA and 0.1 ml was added to separate chamber wells after serial dilution and added to wells for up to 24 hours. The final S1P) concentrations ranged from 1 µM to 32 nM.

Analysis of Human ApoM-IgG1 Fc (hApoM-Fc) and Mouse ApoM-IgG1Fc (mApoM-Fc-S1P) by GPCR "Nanobit" Assay Human 293A cells were dispersed into 6-well culture plates (VWR) at 40,000 cells/well in DMEM supplemented with 10% Fetal Bovine Serum and maintained at 37° C./5% CO2 overnight. Medium was replaced. A transfection reaction was created containing either mammalian expression plasmids encoding. FIG. 5A: S1P1 (200 ng) and Gi-alpha Small bit (200 ng/well), G-beta (500 ng/well), and G-gamma Large bit (500 ng/well) or FIG. 5B: S1P1 (Small-bit; 300 ng/well) and Beta-arrestin (Largebit; 100 ng/well). Both reactions were mixed PEI (Polyethelenimine; 25 mM) for 15 minutes at RT and dripped onto cells. Transfection was incubated at 37° C./5% Co2 for 24 hours. After 24 hours, cells were harvested and dispersed into 96-well plates (White Cellstar, Grenier Bio-one) and incubated with Luciferase substrate (Coelenterazine 50 µM, Sigma). After hours in darkness, the cells were stimulated with Human ApoMFc-S1P, Mouse ApoMFc-S1P, or BSA-S1P or controls with final concentration range from 1000 nM-0.3 nM (S1P).

Blocking/Sponge Assay

The S1P1-beta-arrestin assay was performed as in FIG. 5B. For this assay, 4 µg of ApoMFc-S1P (250 nM S1P) was assayed alone or in combination with 4, 8, or 16 µg of ApoM-Fc, or 16 µg of ApoM-Fc was assayed alone.

REFERENCES

1. Proia, R. L. & Hla, T. Emerging biology of sphingosine-1-phosphate: its role in pathogenesis and therapy. The Journal of clinical investigation 125, 1379-1387, doi: 10.1172/JCI76369 (2015).
2. Frej, C. et al. Sphingosine 1-phosphate and its carrier apolipoprotein M in human sepsis and in *Escherichia coli* sepsis in baboons. Journal of cellular and molecular medicine 20, 1170-1181, doi:10.1111/jcmm.12831 (2016).
3. Ruiz, M. et al. High-Density Lipoprotein-Associated Apolipoprotein M Limits Endothelial Inflammation by Delivering Sphingosine-1-Phosphate to the Sphingosine-1-Phosphate Receptor 1. Arteriosclerosis, thrombosis, and vascular biology 37, 118-129, doi:10.1161/ATVBAHA.116.308435 (2017).
4. Levkau, B. HDL-S1P: cardiovascular functions, disease-associated alterations, and therapeutic applications. Frontiers in pharmacology 6, 243, doi:10.3389/fphar.2015.00243 (2015).
5. Sattler, K. et al. Defects of High-Density Lipoproteins in Coronary Artery Disease Caused by Low Sphingosine-1-Phosphate Content: Correction by Sphingosine-1-Phosphate-Loading. Journal of the American College of Cardiology 66, 1470-1485, doi:10.1016/j.jacc.2015.07.057 (2015).
6. Christoffersen, C. et al. Endothelium-protective sphingosine-1-phosphate provided by HDL-associated apolipoprotein M. Proceedings of the National Academy of Sciences of the United States of America 108, 9613-9618, doi:10.1073/pnas.1103187108 (2011).
7. Pyne, N. J. & Pyne, S. Sphingosine 1-phosphate and cancer. Nat Rev Cancer 10, 489-503, doi:10.1038/nrc2875 (2010).
8. Kitano, M. et al. Sphingosine 1-phosphate/sphingosine 1-phosphate receptor 1 signaling in rheumatoid synovium: regulation of synovial proliferation and inflammatory gene expression. Arthritis Rheum 54, 742-753, doi:10.1002/art.21668 (2006).
9. Michaud, J., Kohno, M., Proia, R. L. & Hla, T. Normal acute and chronic inflammatory responses in sphingosine kinase 1 knockout mice. FEBS Lett 580, 4607-4612, doi:10.1016/j.febslet.2006.07.035 (2006).
10. Smith, L. E. et al. Oxygen-induced retinopathy in the mouse. Investigative ophthalmology & visual science 35, 101-111 (1994).
11. Kho A T, Liu K, Visner G, Martin T, Boudreault F. Identification of dedifferentiation and redevelopment phases during post pneumonectomy lung growth. Am J Physiol Lung Cell Mol Physiol. 2013. October; 305(8): L542 LP-L554.

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A method of decreasing the severity of one or more symptoms associated with bronchopulmonary dysplasia (BPD) or congenital diaphragmatic hernia (CDH), the method comprising administering to a subject in need thereof a therapeutically effective amount of a fusion protein comprising an apolipoprotein M (ApoM) fused to a constant region (Fc) of an immunoglobulin G (lgG), wherein the ApoM comprises the amino acid sequence of SEQ ID NO: 5 or SEQ ID NO: 6, wherein the Fc comprises an amino acid sequence that is 96% identical to SEQ NO 7 or SEQ ID NO: 8.

2. The method of claim 1, wherein the fusion protein further comprises a signal peptide fused to the ApoM.

3. The method of claim 1, wherein the ApoM is fused at the N-terminus of the Fc.

4. The method of claim 1, wherein the ApoM comprises the amino acid sequence of SEQ ID NO: 5.

5. The method of claim 1, wherein the fusion protein comprises an amino acid sequence that is at least 96% identical to any one of SEQ ID NOs: 1-4 and 9.

6. The method of claim 1, wherein the fusion protein is cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combinations thereof.

7. The method of claim 1, wherein the fusion protein activates a SIP receptor.

8. The method of claim 1, wherein the fusion protein is administered intravenously, intranasally, intratracheally, intramuscularly, or by inhalation.

9. The method of claim 1, wherein the subject is human, and the ApoM comprises the amino acid sequence of SEQ ID NO:5 and the Fc comprises the amino acid sequence of SEQ ID NO 7.

10. The method of claim 9, wherein the fusion protein is administered to the human subject in utero, within one hour to one year after birth, or when the human subject is an adult.

11. A method of decreasing the severity of one or more symptoms associated with Bronchopulmonary Dysplasia (BPD), the method comprising administering to a human subject in need thereof a therapeutically effective amount of a fusion protein comprising an apolipoprotein M (ApoM) fused to a constant region (Fc) of an immunoglobulin G (IgG), wherein the ApoM comprises the amino acid sequence of SEQ ID NO: 5, and wherein the Fc comprises the amino acid sequence of SEQ ID NO 7.

12. The method of claim 11, wherein the human subject was born prematurely or was exposed to hyperoxia as a newborn.

13. The method of claim 11, wherein the fusion protein is administered to the human subject in utero, within one hour to one year after birth, or when the human subject is an adult.

14. The method of claim 11, wherein the fusion protein restores lung architecture.

15. A method of decreasing the severity of one or more symptoms associated with Congenital Diaphragmatic Hernia (CDH), the method comprising administering to a human subject in need thereof a therapeutically effective amount of a fusion protein comprising an apolipoprotein M (ApoM) fused to a constant region (Fc) of an immunoglobulin G (IgG), wherein the ApoM comprises the amino acid sequence of SEQ ID NO: 5, and wherein the Fc comprises the amino acid sequence of SEQ ID NO 7.

16. The method of claim 15, wherein the fusion protein is administered to the human subject in utero, within one hour to one year after birth, or when the human subject is an adult.

17. The method of claim 15, wherein the fusion protein increases lung regeneration and growth, and/or restores lung development.

18. The method of claim 1, wherein the one or more symptoms associated with BPD or CDH are selected from the group consisting of: bluish skin, chronic cough, rapid breathing, and shortness of breath.

19. The method of claim 5, wherein the fusion protein comprises an amino acid sequence that is at least 99% identical to the amino acid sequence of SEQ ID NO: 1.

20. The method of claim 19, wherein the fusion protein comprises the amino acid sequence of SEQ ID NO: 1.

21. The method of claim 5, wherein the fusion protein comprises the amino acid sequence of any one of SEQ ID NOs: 1-4 and 9.

22. The method of claim 4, wherein the Fc comprises an amino acid sequence that is at least 99% identical to the amino acid sequence of SEQ ID NO: 7.

* * * * *